United States Patent
Vidra et al.

(10) Patent No.: US 11,952,669 B2
(45) Date of Patent: *Apr. 9, 2024

(54) COMPOSITIONS AND METHODS FOR CREATING NANOSCALE SURFACE GEOMETRIES ON METALS OF AN IMPLANTABLE DEVICE

(71) Applicant: TECH MET, INC., Glassport, PA (US)

(72) Inventors: Michael Vidra, Export, PA (US);
Daniel Jon Schutzer, Irwin, PA (US);
Jordan Incerpi, Pittsburgh, PA (US)

(73) Assignee: Tech Met, Inc., Glassport, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/525,203

(22) Filed: Nov. 12, 2021

(65) Prior Publication Data

US 2022/0145474 A1    May 12, 2022

Related U.S. Application Data

(60) Provisional application No. 63/112,979, filed on Nov. 12, 2020.

(51) Int. Cl.
| | |
|---|---|
| *C23F 1/28* | (2006.01) |
| *A61L 27/04* | (2006.01) |
| *A61L 27/06* | (2006.01) |
| *A61L 27/36* | (2006.01) |
| *A61L 27/50* | (2006.01) |
| *C23F 1/30* | (2006.01) |

(52) U.S. Cl.
CPC ............. *C23F 1/28* (2013.01); *A61L 27/042* (2013.01); *A61L 27/047* (2013.01); *A61L 27/06* (2013.01); *A61L 27/365* (2013.01); *A61L 27/50* (2013.01); *C23F 1/30* (2013.01)

(58) Field of Classification Search
CPC ...... C23F 1/28; C23F 1/30; C23F 1/16; C23F 1/26; C23F 1/32; C23F 1/36; C23F 1/38; C23F 1/02; A61L 27/042; A61L 27/047; A61L 27/06; A61L 27/365; A61L 27/50; A61L 2400/12; A61L 2400/16; A61L 2400/18; A61L 31/022; A61L 31/14; C25F 3/06; C25F 3/14

USPC ................................ 216/108; 252/79.1–79.3
See application file for complete search history.

(56) References Cited

U.S. PATENT DOCUMENTS

| | | | |
|---|---|---|---|
| 3,689,417 A * | 9/1972 | Oikawa ..................... | C23F 1/42 252/79.3 |
| 11,005,884 B2 * | 5/2021 | Gobriel ............... | H04L 63/1458 |
| 2003/0209293 A1 * | 11/2003 | Sako ........................ | C23C 22/44 148/273 |
| 2004/0167633 A1 * | 8/2004 | Wen ...................... | B22F 3/1134 623/23.57 |
| 2020/0190671 A1 * | 6/2020 | Vidra ......................... | C23F 1/04 |
| 2021/0062347 A1 * | 3/2021 | Vidra .................... | A61L 27/045 |

OTHER PUBLICATIONS

Aperam, what is stainless steel? (Year: 2023).*
Wikipedia, Zirconium dioxide (Year: 2013).*
American Elements, Zircyonyl nitrate (Year: 2023).*

* cited by examiner

*Primary Examiner* — Duy Vu N Deo
(74) *Attorney, Agent, or Firm* — Dentons Cohen & Grigsby P.C.

(57) ABSTRACT

Compositions and methods for etching a nanoscale geometry on a metal or metal alloy surface are disclosed. Such surfaces, when included on an implantable medical device, enhance healing after surgery. When included on a bone contacting medical implant, the nanoscale geometry may enhance osseointegration. When included on a tissue contacting device, the nanoscale geometry may enhance endothelial cell attachment, proliferation, and restoration of a healthy endothelial surface.

19 Claims, No Drawings

COMPOSITIONS AND METHODS FOR CREATING NANOSCALE SURFACE GEOMETRIES ON METALS OF AN IMPLANTABLE DEVICE

CROSS-REFERENCE TO RELATED APPLICATIONS

This application claims priority to U.S. Provisional Patent Application Ser. No. 63/112,979 filed Nov. 12, 2020, which is incorporated herein by reference in its entirety.

TECHNICAL FIELD

This invention pertains generally to methods for creating nanoscale geometries on metals and metal alloy surfaces, and more specifically to novel chemistries and methods for creating nanoscale surface geometries on tissue-contacting and bone-contacting surfaces of implantable devices.

BACKGROUND

Tissue contacting implants such as stents were developed to treat various vascular conditions and blockages and to provide an alternative to highly invasive, life-threatening surgeries, particularly in the treatment of coronary artery disease and blocked carotid arteries. A typical stent is a mesh-like tube used to support the vessel wall after minimally invasive treatments such as balloon angioplasty. Typical stent materials include stainless steel, cobalt-nickel, or nickel titanium, i.e., nitinol. In most cases, the metal stent is produced by a three-step process that includes laser cutting followed by chemical (acidic) etching and electropolishing.

The final electropolishing step is generally included to lessen restenosis, i.e., when the body coats the stent with scar tissue and relocks the treated vessel. The smooth surface enhances biocompatibility as it influences the amount of protein adherence, determined by the contact area of the stent with the artery. The smooth surface also eases insertion and travel through the tortuous vessel pathway prior to implantation, and reduces activation and aggregation of platelets, which is recognized as one component of the thrombosis process. As such, the surface properties of a stent determine post stent implantation complications like thrombogenicity and tissue reaction. The optimal stent is engineered to be highly deliverable, to inhibit vascular smooth muscle proliferation and generation of extracellular matrix proteins, and to enhance endothelial attachment, proliferation, and restoration of a healthy endothelial surface.

The optimal surface has been found to be absent micron-sized particles or surface geometry as this encourages neointimal tissue formation. Currently available stents, therefore, frequently include coatings such as hydroxyapatite or nanoporous aluminum oxide over a base material. These coatings provide a nano-sized geometry that has been found to enhance endothelial regeneration. These coatings, however, have been observed to eject nanoparticle debris that can trigger inflammation and subsequent restenosis. Thus, improved methods for providing a nanoscale geometry on tissue contacting surfaces of medical implants is an object of the present invention.

Bone contacting implants such as surgical bone fixation devices, i.e., wires, nails, screws, staples, rods, and plates, have been in clinical use for decades and have generally evolved from industrial designs for fastening wood, steel, plastic, and other materials. Starting in the 1950s, Per-Ingvar Branemark and others demonstrated that implanted bone fixation devices made of pure titanium had the ability to become permanently incorporated with living bone tissue. That is, the living bone tissue becomes so fused with the titanium oxide layer of the implant that the two cannot be separated without fracture. Bone fixation devices formed from pure titanium and its various alloys are the basis for modern skeletal fixation techniques that support healing and functional repair of the human body.

Such bone fixation devices or implants are typically made of elemental metals such as titanium, tantalum, niobium, zirconium and related alloys, certain types of stainless steel, and cobalt-chrome alloys. While all show good mechanical strength and biocompatibility, certain metals and alloys lack an ability to form direct bonds to newly formed bone tissue in the body. As a result, these metals rub against the bones into which they have been implanted, creating wear and tear that shortens the implant lifetimes.

As with tissue contacting devices, i.e., stents and valves, substantial data exists that strongly suggests manipulation of the material surface of a surgical bone fixation device can influence the rate and characteristics of the body's cellular response to the device, and thus the healing process. For example, differentiation of human bone marrow derived cells was found to accelerate on a titanium surface having a nanoscale geometry created by acid etching. Human mesenchymal stem cells, a small population of cells found in adult bone marrow, were found to express markers of an osteoblastic phenotype on an acid etched titanium surface to a greater level than on a non-etched titanium surface. Thus, titanium surfaces having a nanoscale geometry have been found to provide an improved substrate for bone growth and integration, i.e., osseointegration.

Surface manipulations of an implantable device are typically performed to create surface features with dimensions (X, Y and Z) in the nanometer range, such as in a size range of 20-2,000 nm, although one or more of the dimensions could be much larger, such as with a long narrow ridge of material.

For implants having a titanium or cobalt chrome surface, for example, the surface features are typically created by mechanical grit-blasting, by etching in solutions of acids, or by some combination of the two. The use of a strong acid to form these surface features is nearly universal. For example, titanium is typically etched through use of concentrated hydrochloric acid (HCl) at or near its boiling point, and cobalt chrome is etched through use of mixtures of concentrated hydrogen peroxide and concentrated hydrochloric acid. Moreover, this latter method is suitable only for superficial removal of cobalt chrome material as the mixture is volatile, depletes quickly, and suffers from aggressive metal-ion driven decomposition of the peroxide.

Use of these acid-based etching solutions for either surface polishing or for the generation of nanoscale surface features has several drawbacks. For example, highly concentrated acids at elevated temperatures pose a significant safety risk to operators and the environment, e.g., through potential environmental emissions. The availability of suitable fabrication materials for the equipment used to complete these processes is significantly reduced, and equipment life is typically lessened as well. Moreover, use of acid solutions can also degrade the structural strength and performance of the native metal due to intergranular attack or through hydrogen pickup and subsequent embrittlement. The inclusion of HCl or other chloride-containing acid solutions compounds these issues further, with the associated susceptibility to interstitial chloride corrosion.

One particularly significant limitation of the high temperature acid solution approach is that the process typically takes place at or near the boiling point of the acid or the mixed acid solution (e.g., 20% HCl in $H_2O$ has boiling point of 110° C.). The desired chemical etch mechanisms that produce the targeted surface geometries do not typically occur at temperatures significantly below the boiling point and are not altered at temperatures significantly above. While this does provide a somewhat stable processing environment, it also limits the surface geometry. That is, the surface geometry is difficult to change with these types of chemistry since they require a very specialized and confined set of conditions for the geometry to form in the first place. Grit-blast conditions preceding the acid etching can alter the resulting etched surface to some extent, and that is the technique typically used to vary surface geometry, though its effects are limited.

Finally, given the harshness of the chemistry, the limited materials of construction, the precision of conditions required for the desired outcomes, the safety and environmental requirements, the necessity of batch processing due to volatility of the components at the operating temperatures, and the potential need for a preparatory grit blast process, the cost of processing by this means is understandably high.

Accordingly, there is need in the art for improved chemistries and methods for surface finishing of medical implants for use in a wide range of body locations and for a wide range of medical interventions. There is also need in the art for improved chemistries and methods for surface finishing of medical implants so that the implants may be more biocompatible and may provide improved healing at the implant site.

SUMMARY

Described herein are alternate chemistries that address the major drawbacks of the prior art and allow for some adjustment or fine-tuning of surface feature geometries on a substrate. Accordingly, the present invention relates to compositions and methods useful for providing a nanoscale geometry on a metal or metal alloy surface, such as a surface of an implantable device.

According to aspects of the present invention, the implantable device may be a tissue contacting device, such as a stent or valve (e.g., heart valve), wherein the nanoscale surface provided by the compositions and methods disclosed herein enhance biocompatibility and reduce complications like thrombogenicity and adverse tissue reaction. Enhanced biocompatibility may include enhanced endothelial attachment, proliferation, and restoration of a healthy endothelial surface, and reduced thrombogenicity and adverse localized tissue reaction.

According to certain aspects, the implantable device may be a bone contacting device, wherein the nanoscale surface provided by the compositions and methods disclosed herein enhance osseointegration. Bone contacting implantable devices include any medical or dental implant for connection to, or positioning adjacent, a bone. For example, surgical bone fixation devices such as wires, nails, pins, screws, staples, rods, and plates, and implants including at least medical implants such as spinal implants, limb prostheses, cochlear prostheses; and dental implants are all implantable devices of the present invention.

The metals that form all or a part of the implantable devices may include any of titanium, an alloy of titanium, tantalum, an alloy of tantalum, aluminum, an alloy of aluminum, cobalt chrome, stainless steel, an Inconel alloy (i.e., Inconel 600, 617, 625, 690, 718, X-750, etc.), zirconia, niobium, and nitinol.

According to aspects of the presently disclosed invention, the nanoscale geometry may be provided on a surface of any of the implantable devices disclosed herein through exposure to an etching composition.

An exemplary first etching composition useful for etching a metal or metal alloy comprises at least one mineral acid, certain component metals of the alloy to be etched, and optionally iron (Fe). For example, when etching nitinol, the component metals may include titanium (Ti), and nickel (Ni). The at least one mineral acid may be selected from hydrochloric acid (HCl), nitric acid ($HNO_3$), sulfuric acid ($H_2SO_4$), iodic acid ($HIO_3$), and hydrofluoric acid (HF). According to certain aspects, the at least one mineral acid comprises hydrofluoric acid (HF), and optionally nitric acid ($HNO_3$).

An exemplary second etching composition useful for etching a metal or metal alloy comprises at least two mineral acids, certain component metals of the alloy to be etched, and iron (Fe). For example, when etching a cobalt chromium molybdenum alloy, the component metals may include chromium (Cr), molybdenum (Mo), and optionally cobalt (Co). The at least two mineral acids may be selected from hydrochloric acid (HCl), nitric acid ($HNO_3$), sulfuric acid ($H_2SO_4$), iodic acid ($HIO_3$), and hydrofluoric acid (HF). According to certain aspects, the at least two mineral acids may comprise nitric acid ($HNO_3$), hydrofluoric acid (HF), and optionally hydrochloric acid (HCl).

An exemplary third etching composition useful for etching a metal or metal alloy comprises at least two mineral acids, and certain component metals of the metal or metal alloy to be etched. For example, when etching a cobalt chromium molybdenum alloy, the component metals may include chromium (Cr), molybdenum (Mo), and optionally cobalt (Co). The at least two mineral acids may be selected from hydrochloric acid (HCl), nitric acid ($HNO_3$), sulfuric acid ($H_2SO_4$), iodic acid ($HIO_3$), and hydrofluoric acid (HF). According to certain aspects, the at least two mineral acids may comprise nitric acid ($HNO_3$), hydrofluoric acid (HF), and optionally hydrochloric acid (HCl).

An exemplary fourth etching composition useful for etching a metal or metal alloy comprises at least two mineral acids, nitrates, certain component metals of the metal or metal alloy to be etched, and optionally iron (Fe). For example, when etching stainless steel, such as SAE 316L stainless steel, the component metals may include chromium (Cr), molybdenum (Mo), nickel (Ni), and optionally iron (Fe). The at least two mineral acids may be selected from hydrochloric acid (HCl), nitric acid ($HNO_3$), sulfuric acid ($H_2SO_4$), phosphoric ($H_3PO_4$), iodic acid ($HIO_3$), and hydrofluoric acid (HF). According to certain aspects, the at least two mineral acids may comprise hydrochloric acid (HCl) and nitric acid ($HNO_3$), and optionally hydrofluoric acid (HF) and phosphoric acid ($H_3PO_4$), with the caveat that the total nitrates is the sum of the nitric acid and any metal nitrates or chemical intermediates thereof in the composition.

An exemplary fifth etching composition comprises one or more alkaline components; one or more chelating agents; and optionally iron (Fe) and/or one or more metal components of the metal or metal alloy to be etched. According to certain aspects, the one or more alkaline components may comprise a metal hydroxide and an amine. According to certain aspects, the one or more alkaline components may comprise only a metal hydroxide. The metal hydroxide may be included in the composition at 5 to 75 wt. %, or from 5 to 50 wt. %, or from 10 to 35 wt. %, or from 18 to 30 wt. %. When included, the amine may be an alkanolamine and may be included in the composition at up to 40 wt. %, such as 2 to 10 wt. %. The one or more chelating agents may comprise a gluconate, which may be included in the composition at from 0.1 to 58 wt. %, or from 1 to 40 wt. %, or from 2 to 10 wt. %. When included the iron and/or one or more metals may comprise up to 10,000 ppm, or up to 5,000 ppm, or from about 70 ppm to about 180 ppm. When the implantable device includes a titanium surface that is to be etched, the additional metal component may include dissolved titanium at up to 100,000 ppm, such as up to 7,000 ppm. When the implantable device includes an aluminum surface that is to be etched, the additional metal component may include dissolved aluminum at up to 100,000 ppm, such as up to 7,000 ppm.

The presently disclosed invention further provides methods for chemical or electrochemical etching a surface of a metal or metal alloy implantable device to provide the nanoscale geometry on at least one surface thereof.

According to aspects of the presently disclosed invention, a first method of generating a nanoscale surface geometry on at least a portion of an implantable device may include preparing or providing any of the aqueous chemical etching compositions disclosed herein; followed by contacting the portion of the implantable device with the aqueous chemical etching composition. According to certain aspects, the alloy material may be contacted with the chemical etching composition at a temperature of from about 20° C. to about 100° C., such as from about 30° C. to about 95° C., or from about 40° C. to about 95° C., or from about 50° C. to about 95° C., or from about 60° C. to about 95° C. According to further aspects, the alloy material may be contacted with the chemical etching composition at a temperature of from about 65° C. to about 90° C., such as from about 80° C. to about 90° C., such as from about 82° C. to about 88° C. Further, the alloy material may be agitated in the chemical etching composition. According to yet further aspects, the alloy material may be contacted with the chemical etching composition at a temperature of from about 20° C. to about 90° C., such as from about 30° C. to about 80° C., such as from about 30° C. to about 70° C. Further, the alloy material may be agitated in the chemical etching composition.

The metal or metal alloy material may be contacted with the chemical etching composition for a time period that is unlimited and based on the depth to which the surface is to be etched. According to certain exemplary aspects, the metal or metal alloy material may be etched for a time period of up to 1000 minutes, such as up to 200 minutes, or 100 minutes, or 50 minutes. According to certain exemplary aspects, the metal or metal alloy material may be etched for a time period of up at least 1 minute, or at least 2 minutes, or 5 minutes, or 10 minutes. Upper- and lower-time limits may be combined such as, for example, to provide an etch time of 1 to 1000 minutes or 5 to 50 minutes.

According to certain aspects of the method, the surface of the implantable device that is to be etched may be activated by exposure to an activation solution just prior to the chemical etching step. An exemplary activation solution includes an aqueous solution of a mineral acid, such as a solution comprising 10% to 100% (v/v) concentrated hydrochloric acid. The activation step may include submerging or spraying the activation solution on the surface of the implantable device that is to be etched within 240 seconds, or 120 seconds, or 60 seconds, or even 30 seconds of the chemical etching step (i.e., etch the surface of the implant no more than 240 seconds after exposure of the implant surface to the activation solution) so that the surface does not dry before the chemical etching step.

According to certain aspects of a second method for generating a nanoscale surface geometry on at least a portion of an implantable device, the implantable device may be submerged in an aqueous electrolyte solution, i.e., electrochemical etchant, wherein the aqueous electrolyte solution comprises 0.01M to 10M of one or more metal salts; and an electric current of 5 Amps/in$^2$ to 100 Amps/in$^2$ is passed through the electrolyte solution between a cathode and an anode, wherein the implantable device acts as the anode or is connected to the anode. The one or more metal salts may be selected from sodium bromide (NaBr), sodium chloride (NaCl), sodium fluoride (NaF), potassium bromide (KBr), potassium chloride (KCl), potassium fluoride (KF), calcium chloride ($CaCl_2$), magnesium chloride ($MgCl_2$), ammonium chloride ($NH_4Cl$), dibasic sodium phosphate ($Na_2HPO_4$), monobasic sodium phosphate ($NaH_2PO_4$), monobasic potassium phosphate ($KH_2PO_4$), dibasic potassium phosphate ($K_2HPO_4$), sodium sulfate ($Na_2SO_4$), potassium sulfate ($K_2SO_4$), ammonium sulfate (($NH_4)_2SO_4$) sodium nitrate ($NaNO_3$), potassium nitrate ($KNO_3$), ammonium nitrate ($NH_4NO_3$), potassium nitrite ($KNO_2$), and mixtures thereof.

According to certain aspects, either of the methods may further include applying a coating which resists chemical or electrochemical etchants to the implantable device; removing a portion of the coating to form a patterned design in the coating on the implantable device or to expose a surface on the implantable device; and applying the chemical or electrochemical etching composition according to any of the aspects disclosed herein. According to certain aspects, the method may further comprise stripping the coating from the implantable device after etching is complete. For the chemical and electrochemical etching methods, the coating may be resistant to the chemical etching composition or may be electrically non-conductive, respectively.

The disclosed invention further provides implantable devices having a defined three-dimensional pattern produced using any of the methods and etching compositions disclosed herein. These surfaces may provide for improved osseointegration and healing after implantation of the device.

DETAILED DESCRIPTION

In the following description, the present invention is set forth in the context of various alternative embodiments and implementations involving novel chemistries and methods for generating nanoscale geometry on a wide range of metal and metal alloy surfaces. While the following description discloses numerous exemplary embodiments, the scope of the present patent application is not limited to the disclosed embodiments, but also encompasses combinations of the disclosed embodiments, as well as modifications to the disclosed embodiments.

Various aspects of the novel chemistry and methods disclosed herein may be illustrated by describing components that are coupled, attached, and/or joined together, or method steps that are linked. As used herein, the terms "coupled", "attached", "linked", and/or "joined" are interchangeably used to indicate either a direct connection between two components or method steps or, where appropriate, an indirect connection to one another through intervening or intermediate components or steps. In contrast, when a component is referred to as being "directly coupled", "directly attached", "directly linked", and/or "directly joined" to another component or method step, there are no intervening elements or steps shown in said examples.

Various aspects of the novel chemistry and methods disclosed herein may be described and illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to."

It must also be noted that as used herein and in the appended claims, the singular forms "a", "an", and "the" include the plural reference unless the context clearly dictates otherwise. For example, although reference is made to "a" metal, "an" alloy, and "the" substrate, one or more of any of these components and/or any other components described herein can be used.

Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and appended claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

"Substantially free", as used herein, is understood to mean inclusive of only trace amounts of a constituent. "Trace amounts" are those quantitative levels of a constituent that are barely detectable and provide no benefit to the functional properties of the subject composition, process, or articles formed therefrom. For example, a trace amount may constitute 1.0 wt. %, 0.5 wt. %, 0.1 wt. %, 0.05 wt. %, or even 0.01 wt. % of a component or constituent of any of the etching chemistries disclosed herein. "Totally free", as used herein, is understood to mean completely free of a component or constituent.

As used herein, the terms "implantable device", "device", and "substrate" may be used interchangeably, and may be understood to include any device that is implanted within the body of a mammal, such as a human, dog, cat, cow, pig, etc. The implantable device may be implanted to replace or repair a part or portion thereof that has worn-out, such as a heart valve or replacement joint, or may be used to ameliorate a condition of the mammal that may benefit for insertion of the implantable device such as a stent.

As used herein, the phrase "defined three-dimensional pattern" generally refers to a nanoscale surface geometry imparted by the chemical etching compositions and methods of the present invention. "Nanoscale surface geometry" and "nanoscale geometry", as used herein, is understood to mean a surface having topological features with size dimensions in the nanoscale range, such as from 1 nm to 5,000 nm, or from 10 nm to 3,000 nm, or from 20 nm to 2,000 nm.

The nanoscale geometry of the present invention, when formed on a surface of an implantable device, may enhance the biocompatibility of the device. As used herein, the term "biocompatible" may be understood to mean that the implanted device may have a medically acceptable degree of biocompatibility, i.e., that the device does not induce, or lessens, undesirable side effects within the body of the recipient. These undesirable side effects include blood clotting, tissue death, tumor formation, allergic reactions, foreign body reaction (rejection) and/or inflammatory reactions.

Unless defined otherwise, all technical and scientific terms used herein have the same meanings as commonly understood by one of ordinary skill in the art.

Alternate chemistries and methods have been developed to address the major drawbacks of the prior art acid etch chemistries, and to allow for some adjustment or fine-tuning of surface feature geometries. These novel etching chemistries may greatly reduce the rates of hydrogen pickup, potential embrittlement, intergranular attack (IGA), and other corrosion of the substrate typical of prior art etching methods.

The compositions disclosed herein provide a means for performing a subtractive process on a substrate surface, i.e., chemical or electrochemical etching, also referred to as chemical or electrochemical machining or milling. Chemical etching may comprise, for example, exposure of select surfaces of an object or implantable device, or the entire implantable device, to the chemical etching compositions disclosed herein for a period of time sufficient to remove a portion of the surface to a desired depth. In electrochemical etching, an electric circuit is established with a suitable cathode fixed at a desired distance from the substrate or surface, which acts as the anode. An electrolyte compatible with both anode and cathode materials is introduced between the cathode and anode, and current is passed through the circuit. Metal ions from the exposed portions of the substrate or surface are dissolved or dislocated into the electrolyte at a rate proportional to the current applied.

Metals and Metal Alloys

Metal and alloys that have a high resistance to corrosion and are generally biologically inert provide good substrates for the methods and compositions of the presently disclosed invention. For example, titanium, cobalt chrome, stainless steel, Inconel, and related alloys, are strong and well suited for the production of implants that are designed to replace bone and to be load bearing for an extended period, if not permanently. Nitinol has several unique properties, including shape memory and superelasticity, that make it an excellent substrate material for stents or other flexible medical implants. Nitinol is also highly corrosion resistant and may find use in dental implants and fixtures.

Exemplary metals and metal alloys useful in the methods of the present invention include at least titanium, a titanium-based alloy, a cobalt-based alloy, a chromium-based alloy, palladium, a palladium-based alloy, tantalum, a tantalum-based alloy, aluminum, an aluminum-based alloy, stainless steel, an Inconel alloy (i.e., Inconel 600, 617, 625, 690, 718, X-750, etc.), zirconia, niobium, nitinol, platinum, a platinum-based alloy, gold, a gold-based alloy, molybdenum, a molybdenum-based alloy, or an alloy comprising any of nickel, iron, and/or magnesium.

The metal or metal alloys disclosed herein may be included as a surface of an implantable device, wherein the methods and composition disclosed herein may be used to form a nanoscale geometry on that surface. The implantable device may be formed entirely of any one or more of these metals or metal alloys or may comprise a surface formed of any of the metals or metal alloys, i.e., a surface formed over another material such as a ceramic or polymeric material.

The compositions and methods disclosed herein are suitable for etching nanoscale geometry on at least titanium and titanium-based alloys. Suitable titanium alloys include, but are not limited to, titanium-aluminum alloys such as the titanium-3-aluminum-2.5-vanadium alloy (Ti-3Al-2.5V) described in, for example, ASTM Standard F2146-01 and the titanium-6-aluminum-4-vanadium (Ti-6Al-4V) alloy described in, for example, ASTM Standard F136-02a. ASTM standards are available in print or electronic media from ASTM International (West Conshohocken, Pa.).

The compositions and methods disclosed herein are also suitable for etching nanoscale geometry on Cobalt-Chromium alloys. Exemplary Cobalt-Chromium-Molybdenum based alloys include, but are not limited to, the Cobalt-28Chromium-6Molybdenum alloy as described in, for example, ASTM Standard F75 (Alloy Casting and Casting Alloy for Surgical Implants), ASTM Standard F799 (Alloy Forgings for Surgical Implants), or ASTM Standard F1537 (Alloys for Surgical Implants). Cobalt-Chromium alloys containing nickel are also suitable, such as the Cobalt-20Chromium-15Tungsten-10Nickel alloy as described in, for example, ASTM Standard F90 (Wrought Alloy for Surgical Implant Applications), or the 35Cobalt-35Nickel-20Chromium-10Molybdenum alloy described in, for example, ASTM Standard F562 (Alloy for Surgical Implant Applications).

The compositions and methods disclosed herein are also suitable for etching nanoscale geometry on zirconia. Zirconia exists as monoclinic (M), cubic (C), and tetragonal (T) forms. At room temperature, zirconia acquires a monoclinic structure and changes into tetragonal phase at 1170° C., followed by a cubic phase at 2370° C. At room temperature these phases are unstable and break into pieces on cooling. The C-phase of pure Zirconia can be stabilized by adding CaO, MgO, and $Y_2O_3$ (Yttrium) resulting in multiphase material called partially stabilized zirconia (PSZ) combining cubic, monoclinic, and tetragonal phases in the order of importance. Tetragonal zirconia polycrystals (TZP), containing tetragonal phase only can be obtained by adding Yttrium at room temperature. Yttria stabilized TZP possesses low porosity, high density, high bending, and compression strength and is suitable for biomedical applications that include the nanoscale surface geometries described herein.

A titanium-zirconium alloy, i.e., Straumann Roxolid, comprising 13%-17% zirconium (TiZr13-17) is found to have better mechanical attributes, such as increased elongation and fatigue strength, than pure titanium and may also provide an excellent substrate for use as an implantable device as disclosed herein.

Stainless steel, in particular SS304, SS316L, 55420J2, SS630 and the like, provides an excellent substrate according to the methods of the present invention. Among those, for example, SS316L may be preferable for its corrosion resistance and performance record when used inside a living body. SS316L generally comprises carbon equal to or less than 0.035% by weight, phosphorus equal to or less than 0.04% by weight, sulfur equal to or less than 0.03% by weight, manganese equal to or less than 2.00% by weight, silicon equal to or less than 0.75% by weight, chromium from 16.00% by weight to 18.00% by weight, nickel from 12.00% by weight to 15.00% by weight, molybdenum from 2.00% by weight to 3.00% by weight, and iron for the remaining portion.

Nickel-titanium alloys such as linear-elastic and/or super-elastic nitinol also provide excellent substrates for use in the present invention. Nitinol is a commonly used alloy of nickel and titanium where the two elements are generally present in roughly equal amounts. Exemplary nitinol alloys may also include a third metal, such as tantalum or chromium at up to 20 atomic percent.

Other nickel alloys such as nickel-chromium-molybdenum alloys (e.g., UNS: N06625 such as INCONEL® 625, UNS N07718 such as INCONEL® 718, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; combinations thereof; and the like; or any other suitable material are also within the scope of the present invention.

Acidic Chemical Etching Compositions

According to certain aspects of the present invention, the metal or metal alloys may be etched with an acidic chemical etching composition to generate a nanoscale geometry. The chemical etching composition may comprise certain component metals of the metal or metal alloy to be etched, one or more mineral acids, and optionally iron (Fe).

A mineral acid is an inorganic acid derived from one or more inorganic compounds. All mineral acids release hydrogen ions when dissolved in water. Suitable examples of mineral acids include, but are not limited to, hydrochloric acid (HCl), nitric acid ($HNO_3$), phosphoric acid ($H_3PO_4$), sulfuric acid ($H_2SO_4$), hydrofluoric acid (HF), iodic acid ($HIO_3$), and hydrobromic acid (HBr).

According to certain aspects of the present invention, the one or more mineral acids in the chemical etching composition may be selected from hydrochloric acid (HCl), nitric acid ($HNO_3$), sulfuric acid ($H_2SO_4$), iodic acid ($HIO_3$), and hydrofluoric acid (HF). According to certain aspects, the chemical etching composition comprises hydrochloric acid (HCl) and nitric acid ($HNO_3$), or hydrofluoric acid (HF) and nitric acid ($HNO_3$). According to certain aspects, the chemical etching composition comprises hydrochloric acid (HCl), nitric acid ($HNO_3$), and hydrofluoric acid (HF).

According to aspects of the present invention, the chemical etching composition also comprises component metals of the metal or metal alloy to be etched. The chemical etching composition may further comprise iron (Fe).

First Acidic Chemical Etching Composition

An exemplary first etching composition useful for etching a metal or metal alloy comprises at least one mineral acid, certain component metals of the metal or metal alloy to be etched, and optionally iron (Fe). The at least one mineral acid may be selected from hydrochloric acid (HCl), nitric acid ($HNO_3$), sulfuric acid ($H_2SO_4$), iodic acid ($HIO_3$), and hydrofluoric acid (HF). According to certain aspects, the at least one mineral acid comprises hydrofluoric acid (HF), and optionally nitric acid ($HNO_3$).

According to certain aspects, the first etching composition comprises 0 g/l-225 g/l iron (Fe) and 0 g/l—saturation of the component metals, such as 3.75 g/l-90 g/l. For example, when etching nitinol, the component metals may include titanium (Ti), nickel (Ni), and optionally iron (Fe). Thus, the component metals for a Ti:Ni nitinol may include 3.75 g/l-90 g/l Ti and 3.75 g/l-90 g/l Ni. According to certain aspects, the component metals may be included in the first etching composition in a relative ratio that corresponds to a ratio of the metals in the metal alloy. According to certain aspects, the component metals may be included in the first etching composition in saturating amounts, wherein a relative ratio of the metals in the etching composition may correspond to a ratio of the metals in the metal alloy.

According to certain aspects, the first etching composition comprises no iron (Fe), or at least 10 g/l, or at least 20 g/l, or at least 30 g/l, or at least 40 g/l, or at least 60 g/l, or at least 80 g/l, or at least 100 g/l, or at least 150 g/l, or at least 200 g/l. According to certain other aspects, the chemical etching composition comprises up to 225 g/l iron (Fe), such as up to 200 g/l, or up to 150 g/l, or up to 125 g/l, or up to 100 g/l, or up to 90 g/l, or up to 70 g/l, or up to 50 g/l, or up to 30 g/l, or up to 20 g/l, or up to 10 g/l.

According to certain other aspects, the first etching composition comprises 0.1N to 43N hydrofluoric acid (HF), and 0N to 15N nitric acid ($HNO_3$). For example, the chemical etching composition may comprise 0.5N to 3.5N hydrofluoric acid (HF), and 0.1N to 3N nitric acid ($HNO_3$).

According to certain aspects, the first etching composition comprises at least 0.5N hydrofluoric acid (HF), such as at least 1.0N, or at least 1.5N, or at least 2.0N, or at least 2.5N, or at least 3.0N. According to certain other aspects, the chemical etching composition comprises up to 3.5N hydrofluoric acid (HF), such as up to 3.0N, or up to 2.5N, or up to 2.0N, or up to 1.5N, or up to 1.0N.

According to certain aspects, the first etching composition comprises at least 0.1N nitric acid ($HNO_3$), such as at least 0.5N, or at least 1.0N, or at least 1.5N, or at least 2.0N, or at least 2.5N. According to certain other aspects, the chemical etching composition comprises up to 3.0 nitric acid ($HNO_3$), such as up to 2.5N, or up to 2.0N, or up to 1.5N, or up to 0.5N.

Second Acidic Chemical Etching Composition

An exemplary second etching composition useful for etching a metal or metal alloy comprises at least two mineral acids, certain component metals of the metal or metal alloy to be etched, and iron (Fe). The at least two mineral acids may be selected from hydrochloric acid (HCl), nitric acid ($HNO_3$), sulfuric acid ($H_2SO_4$), iodic acid ($HIO_3$), and hydrofluoric acid (HF). According to certain aspects, the at least two mineral acids may comprise nitric acid ($HNO_3$), hydrofluoric acid (HF), and optionally hydrochloric acid (HCl).

According to certain other aspects, the second etching composition comprises 0.1N to 2.0N hydrofluoric acid (HF), 1N to 10N hydrochloric (HCl), and 0.05N to 0.8N nitric acid ($HNO_3$).

According to certain aspects, the second etching composition comprises at least 1N hydrochloric acid (HCl), such as at least 1.5N, or at least 2.0N, or at least 3.0N, or at least 3N, or at least 3.5N, or at least 4N, or at least 4.5N, or at least 5N, or at least 5.5N, or at least 6N, or at least 6.5N, or at least 7N, or at least 7.5N, or at least 8N, or at least 8.5N, or at least 9N, or at least 9.5, or even up to 10N. According to certain other aspects, the chemical etching composition comprises up to 9.5N hydrochloric acid (HCl), such as up to 9N, or up to 8N, or up to 7N, or up to 6N, or up to 5N, or up to 4N, or up to 3N, or up to 2N. Any combination of upper and lower amounts listed herein are possible, such as from 2N to 10N HCL.

According to certain aspects, the second etching composition comprises at least 0.05N nitric acid ($HNO_3$), such as at least 0.1N, or at least 0.2N, or at least 0.3N, or at least 0.4N, or at least 0.5N, or at least 0.6N, or at least 0.7N. According to certain other aspects, the chemical etching composition comprises up to 0.8 nitric acid ($HNO_3$), such as up to 0.7N, or up to 0.6N, or up to 0.5N, or up to 0.4N, or up to 0.3N, or up to 0.2N. Any combination of upper and lower amounts listed herein are possible, such as from 0.05N to 0.3N $HNO_3$.

According to certain aspects, the second chemical etching composition comprises at least 0.1N hydrofluoric acid (HF), such as at least 0.2N, or at least 0.3N, or at least 0.4N, or at least 0.5N, or at least 0.6N, or at least 0.7N, or at least 0.8N, or at least 0.9N, or at least 1.0N, or at least 1.1N, or at least 1.2N. According to certain other aspects, the chemical etching composition comprises up to 2.0N hydrofluoric acid (HF), such as up to 1.8N, or up to 1.6N, or up to 1.4N, or up to 1.2N, or up to 1.1N, or up to 1.0N, or up to 0.9N, or up to 0.8N, or up to 0.7N, or up to 0.6N, or up to 0.5N. Any combination of upper and lower amounts listed herein are possible, such as from 0.1N to 0.8N HF.

The concentrations of acids and component metals may be varied with varied amounts of iron. Exemplary formulations for etching cobalt chrome with the second etching composition are shown in Tables I and II of the examples.

According to certain aspects, the second etching composition comprises 0.1 g/l-225 g/l iron (Fe) and 0 g/l-400 g/l of the component metals. For example, when etching an ASTM F75 cobalt chrome, the component metals may include chromium (Cr), molybdenum (Mb), and optionally cobalt (Co). Thus, the component metals may be included as 0.0 g/l to 400 g/l cobalt, 0.1 g/l to 400 g/l molybdenum, and 0.2 g/l to 400 g/l chromium.

According to certain aspects, when etching cobalt chrome using the second etching composition, the composition comprises at least 0.2 g/l chromium (Cr), such as at least 0.3 g/l, or at least 1 g/l Cr, or at least 2 g/l, or at least 3 g/l, or at least 4 g/l, or at least 5 g/l, or at least 6 g/l, or at least 7 g/l, or at least 8 g/l, or at least 9 g/l. The chemical etching compositions may comprise up to 400 g/l Cr, such as up to 350 g/l Cr, or up to 300 g/l, or up to 250 g/l, or up to 200 g/l, or up to 150 g/l, or up to 100 g/l, or up to 50 g/l, or up to 20 g/l. The chemical etching compositions may comprise Cr in any combination of upper and lower limits listed herein, such as, for example, from 0.2 g/l to 400 g/l, such as from 0.2 g/l to 300 g/l, or from 0.2 g/l to 200 g/l, or from 0.2 g/l to 100 g/l Cr, etc.

According to certain aspects, when etching cobalt chrome using the second etching composition, the composition comprises at least 0.1 g/l molybdenum (Mo), such as at least 0.5 g/l Mo, or at least 1 g/l, or at least 2 g/l, or at least 3 g/l, or at least 4 g/l Mo. The chemical etching compositions disclosed herein generally comprise up to 400 g/l Mo, such as up to 350 g/l, or up to 300 g/l, or up to 200 g/l, or up to 100 g/l, or up to 50 g/l. The chemical etching compositions may comprise Mo in any combination of upper and lower limits listed herein, such as, for example, from 0.1 g/l to 400 g/l, such as from 0.1 g/l to 300 g/l, or from 0.1 g/l to 200 g/l, or from 0.1 g/l to 100 g/l Mo, etc.

According to certain aspects, when etching a cobalt chrome using the second etching composition, the composition comprises no cobalt (Co), or at least 0.1 g/l, or at least 1 g/l, or at least 2 g/l, or at least 4 g/l, or at least 6 g/l, or at least 8 g/l, or at least 10 g/l, or at least 15 g/l, or at least 20 g/l Co. According to certain aspects, the chemical etching composition comprises up to 400 g/l Co, such as up to 350 g/l Co, or up to 300 g/l, or up to 250 g/l, or up to 200 g/l, or up to 150 g/l, or up to 100 g/l, or up to 50 g/l, or up to 20 g/l Co. When Co is included, the chemical etching compositions may comprise Co in any combination of upper and lower limits listed herein, such as, for example, from 0.1 g/l to 400 g/l, such as from 2 g/l to 300 g/l, or from 2 g/l to 50 g/l, or from 4 g/l to 20 g/l Cr, etc.

Without being tied to one theory, it is believed that the addition of iron to the chemical etching composition may help to stabilize the reaction rate of the composition. Accordingly, the chemical etching compositions may comprise at least 10 g/l iron (Fe), such as at least 20 g/l Fe, or at least 30 g/l, or at least 50 g/l, or at least 70 g/l, or at least 90 g/l, or at least 110 g/l, or at least 130 g/l, or at least 150 g/l, or at least 170 g/l, or at least 200 g/l Fe. The chemical etching compositions may comprise up to 400 g/l Fe, such as up to 350 g/l Fe, or up to 300 g/l, or up to 250 g/l, or up to 200 g/l, or up to 150 g/l, or up to 100 g/l, or up to 50 g/l, or up to 20 g/l Fe. When Fe is included, the chemical etching compositions may comprise Fe in any combination of upper and lower limits listed herein, such as, for example, from 0.1 g/l to 400 g/l Fe, such as from 2 g/l to 225 g/l Fe, or from 20 g/l to 50 g/l, or from 50 g/l to 225 g/l Fe, etc.

Third Acidic Chemical Etching Composition

An exemplary third etching composition useful for etching a metal or metal alloy comprises at least two mineral acids, and certain component metals of the metal or metal alloy to be etched. The at least two mineral acids may be selected from hydrochloric acid (HCl), nitric acid ($HNO_3$), sulfuric acid ($H_2SO_4$), iodic acid ($HIO_3$), and hydrofluoric acid (HF). According to certain aspects, the at least two mineral acids may comprise nitric acid ($HNO_3$), hydrofluoric acid (HF), and optionally hydrochloric acid (HCl).

According to certain aspects, the third etching composition may comprise 0.1N to 2.0N hydrofluoric acid (HF), 1N to 10N hydrochloric (HCl), and 0.05N to 0.8N nitric acid ($HNO_3$).

According to certain aspects, the third etching composition comprises at least 1N hydrochloric acid (HCl), such as at least 1.5N, or at least 2.0N, or at least 3.0N, or at least 3N, or at least 3.5N, or at least 4N, or at least 4.5N, or at least 5N, or at least 5.5N, or at least 6N, or at least 6.5N, or at least 7N, or at least 7.5N, or at least 8N, or at least 8.5N, or at least 9N, or at least 9.5, or even up to 10N. According to certain other aspects, the chemical etching composition comprises up to 9.5N hydrochloric acid (HCl), such as up to 9N, or up to 8N, or up to 7N, or up to 6N, or up to 5N, or up to 4N, or up to 3N, or up to 2N. Any combination of upper and lower amounts listed herein are possible, such as from 2N to 10N HCL.

According to certain aspects, the third etching composition comprises at least 0.05N nitric acid ($HNO_3$), such as at least 0.1N, or at least 0.2N, or at least 0.3N, or at least 0.4N, or at least 0.5N, or at least 0.6N, or at least 0.7N. According to certain other aspects, the chemical etching composition comprises up to 0.8 nitric acid ($HNO_3$), such as up to 0.7N, or up to 0.6N, or up to 0.5N, or up to 0.4N, or up to 0.3N, or up to 0.2N. Any combination of upper and lower amounts listed herein are possible, such as from 0.05N to 0.3N $HNO_3$.

According to certain aspects, the third chemical etching composition comprises at least 0.1N hydrofluoric acid (HF), such as at least 0.2N, or at least 0.3N, or at least 0.4N, or at least 0.5N, or at least 0.6N, or at least 0.7N, or at least 0.8N, or at least 0.9N, or at least 1.0N, or at least 1.1N, or at least 1.2N. According to certain other aspects, the chemical etching composition comprises up to 2.0N hydrofluoric acid (HF), such as up to 1.8N, or up to 1.6N, or up to 1.4N, or up to 1.2N, or up to 1.1N, or up to 1.0N, or up to 0.9N, or up to 0.8N, or up to 0.7N, or up to 0.6N, or up to 0.5N. Any combination of upper and lower amounts listed herein are possible, such as from 0.1N to 0.8N HF.

According to certain aspects, the third etching composition comprises 1 g/l-400 g/l (e.g., saturation) of the component metals. For example, when etching an ASTM F75 cobalt chrome, the component metals may include chromium (Cr), molybdenum (Mb), and optionally cobalt (Co) as indicated hereinabove for the second acidic chemical etching composition. In an exemplary formulation, the component metals may be included as 0.0 g/l to 355 g/l cobalt, 0.1 g/l to 40 g/l molybdenum, and 0.2 g/l to 170 g/l chromium. In an exemplary formulation, the component metals may be included as 7 g/l to 355 g/l cobalt, 1 g/l to 40 g/l molybdenum, and 3 g/l to 170 g/l chromium. An exemplary formulation is shown in Table III in the examples.

Fourth Acidic Chemical Etching Composition

An exemplary fourth etching composition useful for etching a metal alloy comprises at least two mineral acids, nitrates, certain component metals of the alloy to be etched, and optionally iron (Fe). The at least two mineral acids may be selected from hydrochloric acid (HCl), nitric acid ($HNO_3$), sulfuric acid ($H_2SO_4$), phosphoric ($H_3PO_4$), iodic acid ($HIO_3$), and hydrofluoric acid (HF). According to certain aspects, the at least two mineral acids may comprise hydrochloric acid (HCl) and nitric acid ($HNO_3$), and optionally hydrofluoric acid (HF) and phosphoric acid ($H_3PO_4$), with the caveat that the total nitrates is the sum of the nitric acid and any metal nitrates or chemical intermediates thereof in the composition.

According to certain aspects, the fourth etching composition may comprise 0.3N to 12N hydrochloric acid (HCl), 0N to 15N nitric acid ($HNO_3$), 0N to 3N phosphoric acid ($H_3PO_4$), and 0N to 43N hydrofluoric acid (HF). According to certain aspects, the fourth etching composition may comprise 1.2N to 3.0N hydrochloric acid (HCl), 2.0N to 4.0N nitric acid ($HNO_3$), 0.1N to 0.3N phosphoric acid ($H_3PO_4$), and 0.1 to 0.3N hydrofluoric acid (HF).

According to certain aspects, the fourth etching composition may comprise at least 1.2N hydrochloric acid (HCl), such as at least 1.4N, or at least 1.6N, or at least 1.8N, or at least 2.0N, or at least 2.2N, or at least 2.4N, or at least 2.6N, or at least 2.8N. According to certain other aspects, the fourth etching composition may comprise up to 2.8N hydrochloric acid (HCl), such as up to 2.6N, or up to 2.4N, or up to 2.2N, or up to 2.0N, or up to 1.8N, or up to 1.6N, or up to 1.4N, or up to 1.2N, or up to 1.0N, or up to 0.8N, or up to 0.6N, or up to 0.4N.

According to certain aspects, the fourth etching composition may comprise at least 2.2N nitric acid ($HNO_3$), such as at least 2.4N, or at least 2.6N, or at least 2.8N, or at least 3.0N, or at least 3.2N, or at least 3.4N, or at least 3.6N, or at least 3.8N. According to certain other aspects, the fourth etching composition may comprise up to 3.8N nitric acid ($HNO_3$), such as up to 3.6N, or up to 3.4N, or up to 3.2N, or up to 3.0N, or up to 2.8N, or up to 2.6N, or up to 2.4N, or up to 2.2N.

According to certain aspects, the fourth etching composition may comprise at least 0.1N phosphoric acid ($H_3PO_4$), such as at least 0.2N, or at least 0.3N. According to certain other aspects, the fourth etching composition may comprise up to 0.3N phosphoric acid ($H_3PO_4$), such as up to 0.2N, or up to 0.3N.

According to certain aspects, the fourth etching composition may comprise at least 0.1N hydrofluoric acid (HF), such as at least 0.2N, or at least 0.3N. According to certain other aspects, the fourth etching composition may comprise up to 0.3N hydrofluoric acid (HF), such as up to 0.2N, or up to 0.3N.

According to certain aspects, the fourth etching composition comprises 0 g/l-225 g/l iron (Fe) and 0 g/l-saturation of the component metals, such as 3.75 g/l-90 g/l. For example, when etching stainless steel, such as SAE 316L stainless steel, the component metals may include chromium (Cr), molybdenum (Mo), and/or nickel (Ni). Thus, the component metals for a 316 stainless steel may include 3.75 g/l-90 g/l for one or more of Cr, Mo, and Ni, or may include 3.75 g/l-90 g/l Cr, 3.75 g/l-90 g/l Mo, and 3.75 g/l-90 g/l Ni. According to certain aspects, the component metals may be included in the fourth etching composition in a relative ratio that corresponds to a ratio of the metals in the metal alloy. According to certain aspects, the component metals may be included in the fourth etching composition in saturating amounts, wherein a relative ratio of the metals in the etching composition may correspond to a ratio of the metals in the metal alloy.

According to certain aspects, the fourth etching composition comprises no iron (Fe), or at least 10 g/l, or at least 20 g/l, or at least 30 g/l, or at least 40 g/l, or at least 60 g/l, or at least 80 g/l, or at least 100 g/l, or at least 150 g/l, or at least 200 g/l. According to certain other aspects, the fourth chemical etching composition comprises up to 225 g/l iron (Fe), such as up to 200 g/l, or up to 150 g/l, or up to 125 g/l, or up to 100 g/l, or up to 90 g/l, or up to 70 g/l, or up to 50 g/l, or up to 30 g/l, or up to 20 g/l, or up to 10 g/l.

Alkaline Chemical Etching Compositions

According to certain aspects of the present invention, the metal or metal alloys may be etched with an alkaline chemical etching composition to generate a nanoscale geometry. The chemical etching composition may comprise one or more alkaline components, combined with one or more complexing or chelating agents, and dissolved metals in solution to moderate and stabilize the rate of reaction.

According to certain aspects, the present invention provides an alkaline composition for etching a substrate comprising a metal hydroxide, one or more chelating agents, dissolved metals, such as iron (Fe) and/or other metals found in the substrate, and optionally an amine. For example, when etching a titanium substrate, the dissolved metals may include dissolved titanium, and when etching an aluminum substrate, the dissolved metals may include dissolved aluminum.

The metal hydroxide(s), such as sodium hydroxide and/or potassium hydroxide, may be included in the etch compositions at from 5 to 75 wt. %, based on the total weight of the composition. According to certain aspects, the metal hydroxide(s) may be included in the composition in an amount of at least 5 wt. %, such as at least 10 wt. %, or at least 15 wt. %, or at least 18 wt. %, or at least 20 wt. %. According to certain aspects, the metal hydroxide(s) may be included in the composition in an amount of up to 75 wt. %, or up to 65 wt. %, or up to 55 wt. %, or up to 45 wt. %, or up to 35 wt. %, or up to 30 wt. %. The metal hydroxide(s) may be included in the composition at any upper and lower amount listed hereinabove. For example, the metal hydroxide(s) may be included in the composition at from 10 to 35 wt. %, or from 18 to 30 wt. %.

In addition to the metal hydroxides, certain compositions may optionally comprise an amine or mixture of amines, such as an alkanolamine or mixture thereof. Exemplary alkanolamines include at least triethanolamine, diethanolamine, ethanolamine, and mixtures such as triethanolamine and diethanolamine. According to certain aspects, the amine(s) may be included in the composition at 0.1 wt. % to 40 wt. %. The amine(s) may be included in the composition at up to 40 wt. %, such as up to 35 wt. %, or up to 30 wt. %, or up to 25 wt. %, or up to 20 wt. %, or up to 15 wt. %, or up to 10 wt. %, or up to 6 wt. %. The amine(s) may be included in the composition in an amount of at least 0.01 wt. %, or at least 0.1 wt. %, or at least 1 wt. %, or at least 2 wt. %, or at least 3 wt. %. The amine(s) may be included in the composition at any upper and lower amount listed hereinabove. For example, the amine(s) may be included in the composition at from 2 wt. % to 10 wt. %, or even from 3 wt. % to 6 wt. %.

According to certain aspects, the composition is substantially free of amine. According to certain aspects, the composition is totally free of amine.

The chemical etching compositions further comprise one or more chelating agents, such as any chelating organic salt or organic acid. Exemplary chelating agents include gluconates, citrates, tartrates, and ethylenediaminetetraacetic acid (EDTA). An exemplary gluconate includes at least sodium gluconate. According to certain aspects, the one or more chelating agents may be included in the composition at 0.1 wt. % to 58 wt. %. The chelating agent(s) may be included in the composition at up to 58 wt. %, such as up to 50 wt. %, or up to 40 wt. %, or to 35 wt. %, or up to 30 wt. %, or up to 25 wt. %, or up to 20 wt. %, or up to 15 wt. %, or up to 10 wt. %, or up to 6 wt. %. The chelating agent(s) may be included in the composition in an amount of at least 0.01 wt. %, or at least 0.1 wt. %, or at least 1 wt. %, or at least 2 wt. %, or at least 3 wt. %. The chelating agent(s) may be included in the composition at any upper and lower amount listed hereinabove. For example, the chelating agent(s) may be included in the composition at from 1 to 40 wt. %, or from 2 to 10 wt. %, or even 3 to 6 wt. %.

According to aspects of the present invention, the composition comprises component metals of the metal or metal alloy to be etched. For example, the chemical etching solution may comprise titanium (Ti) when used to etch a titanium implantable device. Alternatively, the chemical etching solution may comprise aluminum (Al) when used to etch an aluminum substrate or implantable device. The component metal(s) may be included in the composition at up to 100,000 ppm, such as up to 50,000 ppm, or up to 20,000 ppm, or up to 10,000 ppm, or up to 8,000 ppm, or up to 7,000 ppm, or up to 6,000 ppm, or up to 5,000 ppm. The component metal(s) may be included in the composition in an amount of at least 1 ppm, or at least 10 ppm, or at least 50 ppm, or at least 100 ppm, or at least 500 ppm, or at least 1,000 ppm. The component metals(s) may be included in the composition at any upper and lower amount listed hereinabove. For example, the component metal(s) may be included in the composition at from about 10 ppm to about 7,000 ppm, or from about 50 ppm to about 7,000 ppm, or from about 100 ppm to about 7,000 ppm, or from about 100 ppm to about 5,000 ppm, or from 500 ppm to 10,000 ppm.

Certain compositions may further comprise iron (Fe). Iron may be included in the chemical etching compositions at up to 10,000 ppm, such as up to 5,000 ppm, or up to 2,000 ppm, or up to 1,000 ppm, or up to 500 ppm, or up to 180 ppm, or up to 100 ppm. Iron may be included in the composition in an amount of at least 1 ppm, or at least 10 ppm, or at least 50 ppm, or at least 70 ppm, or at least 100 ppm. The iron may be included in the composition at any upper and lower amount listed hereinabove. For example, the iron may be included in the composition at from about 10 ppm to about 500 ppm, or from about 70 ppm to about 180 ppm.

According to certain aspects, the composition is substantially free of added iron, or even substantially free of iron. According to certain aspects, the composition is totally free of added iron, or even totally free of iron.

According to certain aspects of the present invention, the total amount of metal(s) included in the composition may be at least 100 ppm, such as from either of the iron or component metals of the metal or metal alloy to be etched. That is, if at least 100 ppm of the component metal is included (e.g., 100 ppm titanium), the composition may include no iron. Alternatively, if at least 100 ppm of iron is included in the composition, the component metal may be optional (e.g., 0 ppm titanium).

The metal component or implantable device may be exposed to the inventive chemical etching compositions at temperatures of about 60° F. to about 280° F. (about 15.5° C. to about 138° C.), such as about 175° F. to about 200° F. (about 80° C. to about 93° C.), for time periods of up to 100 hours, such as at least 1 minute to 10 hours, or from 10 minutes to 60 minutes.

An exemplary alkaline etching composition comprises one or more alkaline components; one or more chelating agents; iron (Fe); and optionally, an additional metal component of the implantable device. According to certain aspects, the one or more alkaline components may comprise a metal hydroxide and an amine. The metal hydroxide may be included in the composition at 5 to 75 wt. %, such as 5 to 50 wt. %, or 10 to 35 wt. %, or even 18 to 30 wt. %. The amine may be an alkanolamine and may be included in the composition at up to 40 wt. %, such as 0.1 wt. % to 40 wt. %. The one or more chelating agents may comprise a gluconate, which may be included in the composition at 0.1 to 40 wt. %, such as 2 to 10 wt. %. The metals may exclude iron, or may include iron, such as up to 10,000 ppm, or up to 5,000 ppm, or from about 70 ppm to about 180 ppm. When the implantable device includes a titanium surface that is to be etched, the additional metal component may include dissolved titanium at up to 100,000 ppm, such as up to 7,000 ppm.

The alkaline etching chemistry is very stable and provides a highly repeatable means for etching a nanoscale geometry into the surface of a titanium or aluminum substrate, such as a surface of an implantable device. The chemistry is compatible with a much wider range of construction materials than prior art acid etch compositions, as long as the operating temperature is accounted for (e.g., 316 stainless steel is an example of a common material that is an appropriate choice for use in the processing equipment for use in the methods of etching with the alkaline etching compositions). Moreover, the alkaline chemical etching compositions are readily scalable and useable in process that are readily automated. This, in addition to the chemical stability of the alkaline composition, work to drive processing costs down.

Methods for Chemical Etching

According to certain aspects of the present invention, the implantable device may be etched on one or more surfaces by contacting at least one surface of the device with any of the acidic or alkaline chemical etching compositions disclosed herein.

Activation of Passivated Surfaces

For certain substrates, the surface may be passivated, i.e., resistant to the etching compositions provided herein. In such a case, the surface may require an activation step. That is, before the implantable device can be etched with the chemical etching compositions of the presently disclosed invention, the surface to be etched may be activated. An exemplary activation step includes exposing the surface to be etched to a mineral acid such as a 10% to 100% solution of concentrated hydrochloric acid (v/v; dilution with an aqueous buffer or water). The surface may be exposed to the mineral acid at a range of temperatures, such as room temperature, wherein higher temperatures generally require lower concentrations of the mineral acid. The implantable device may be exposed to the mineral acid by submersion or spraying.

Immediately after activation, such as within 120 seconds, or 60 seconds, or 30 seconds, the implantable device may be exposed to the chemical etching compositions as described herein below. According to certain aspects, the device may still be "wet" with the activation solution (i.e., mineral acid such as the 10%-100% dilution of hydrochloric acid).

Etching Using an Alkaline or Acidic Etching Composition

After the surface of the implantable device is activated, when required, it may be etched by contacting the implantable device with the chemical etching compositions, which may include dipping or submersing the device, or at least a portion of one surface thereof, in the composition, or spraying, rolling, or brushing the composition onto one or more surfaces of the implantable device. For example, the part to be etched may be attached to a fixture resistant to the chemical etch composition and both the part and at least a portion of the fixture may be submerged in the chemical etch composition for a specified time (e.g., the part is suspended over/in the chemical etch composition).

The present inventors have found that it may be preferred to position the surfaces to be etched horizontally, such as facing upward in the solution, or vertically depending on the targeted surface characteristics. The gaseous byproducts of the etch reaction move directly upwards and away from the surface when that surface is etched horizontally, and do not otherwise affect the process. When the surface to be etched is positioned vertically, bubbles may travel along the vertical surface and influence the etch rate through localized microcirculation and its effects on the replenishment of unreacted chemistry to the target surface. In such ways, surface geometry may be manipulated by adjusting the angle of the parts (with respect to horizontal) during processing.

Thus, according to certain aspects of the present invention, the implantable device may be etched on one or more surfaces by positioning the device at an angle within the chemical etching composition. Exemplary angles include 0° with respect to the surface of the "bath" containing the chemical etch composition (i.e., horizontal facing upward), to 90° with respect to the surface of the bath (i.e., vertical), to 180° with respect to the surface of the bath (i.e., horizontal facing downward), or any angle therebetween.

Alternatively, the part may be placed into a perforated or mesh drum that is then submerged within the chemical etch composition, and the drum may be rotated to allow for random or semi-random movement of the part while processing. Additional substrate, such as inert plastic beads or pieces, may be added to the drum to cushion the parts during rotation.

The chemical treating step may include agitating the implantable device in the chemical etching composition. The chemical treating step may include recirculating the etching composition, wherein the recirculating may include circulation of the original chemical etching solution (i.e., etching solution applied/used at start of method), or circulation of the original chemical etching solution with additional new, unused chemical etching solution. The chemical treating step may include exchange of used chemical etching solution after a certain amount of etch time for new, unused chemical etch solution.

The chemical treating step may further include heating the implantable device and/or the chemical etching composition. For the acidic chemical etching compositions, the implantable device may be heater to a temperature in a range of from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 88° C. According to certain aspects, the alloy material may be contacted with the chemical etching composition at a temperature in a range of from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 88° C.

Alternatively, for the alkaline chemical etching compositions, the implantable device may be exposed to the etching compositions at temperatures of about 60° F. to about 280° F. (about 15.5° C. to about 138° C.), such as about 175° F. to about 200° F. (about 80° C. to about 93° C.

According to certain aspects, the alloy material may be contacted with the chemical etching composition for an unlimited time period based on the desired depth of etch. Etching starts as soon as the alloy material is exposed to the chemical etching composition and may proceed until the desired depth of etching is achieved. As such, the alloy material may be contacted with the chemical etching compositions from greater than 0 seconds to several hours or days. According to certain aspects of the presently disclosed invention, the alloy material may be exposed to, such as agitated within, the chemical etching composition for a time of from 1 to 1000 minutes, such as from 2 to 200 minutes, or from 5 to 50 minutes.

The chemical etching methods may be used to remove portions or all of a surface of the implantable device to a desired depth. Moreover, the compositions and methods disclosed herein provide removal of the material without significant intergranular attack (IGA). The compositions and methods disclosed herein also provide means to remove or reduce debris from the implantable device surfaces, such as artifacts of the additive manufacturing process, e.g., powder, particles, granules, etc. that were not completely melted or completely sintered during the additive building. Debris may also include external debris such as dirt or other artifacts of handling.

The chemical etching compositions and methods of the present invention may be used to etch a metal or metal alloy substrate, leaving a surface having nanoscale geometry. As mentioned, these inventive compositions and methods allow fine adjustment of the surface geometry by varying the amounts of various components in the composition, and/or the time and temperature of exposure, either in unison or relative to one another. That is, the concentrations of the various components may be raised in unison, such as by addition of components or evaporation; lowered in unison, such as by addition of aqueous solvent; or changed individually. Additionally, the time and temperature of exposure may be varied with changes in the chemistry, or with changes in either of the variables (e.g., increased exposure time at lowered reaction temperatures).

The amount of material removed by the chemical etching composition, i.e., the depth of the etch, is unlimited and may depend on the amount of exposure time to the chemical etching composition and depletion of the chemistry in the composition, e.g., after long exposure times.

The rate of etching, i.e., rate of material removed, may depend on a combination of the proportion of chemical components to one another, the temperature, and/or amount of agitation of the implantable device in the chemical etching composition. For example, according to certain aspects of the presently disclosed methods, a metal or metal alloy substrate may be etched at a rate of 0.1 to 1 mil/minute in the presently disclosed chemical etching compositions, such as 0.3 to 1 mil/minutes, or about 0.5 mil/minute, when exposed at room temperature.

Once etching is complete, the implantable device may be rinsed clean of all residual etchant and, if a coating is present on the implantable device to protect certain surfaces, placed in a bath of stripping solution (a solvent matched to the coatings) to remove all remaining coating material.

One unique and unexpected quality of certain of the etching compositions and methods of the presently disclosed invention is that the final surface, after the chemical etching is completed, may be a passivated surface. That is, the etched implantable device may be resistant to etching a subsequent time. Alternate chemistries, such as the activation chemistry described herein above, and/or mechanical polishing or abrasion may be used to fracture, disrupt, or activate the passivated surface in preparation for a subsequent round of chemical etching using the chemical etching compositions of the present invention.

These passivated surfaces have lower surface reactivity, which may thus lower the overall toxicity of the alloy in the human body. Moreover, passivation may be useful to achieve complex patterning of a surface, where certain areas that are protected during a first round of etching, may be uncoated and etched during a second round of etching to a depth different than the depth of etching achieved during the first round of etching. Such a process may be used to achieve any number of varied depths in a substrate over any number of coating and etching processes. In addition, the resultant surface may be expected to exhibit an even higher degree of corrosion resistance at elevated temperatures that the pre etch base alloy.

Electrochemical Etching Compositions and Methods

An electrochemical etching (EChE) process may be used to provide the nanoscale surface geometry. The device may be submerged in an electrolytic solution and may have a cathode inserted in the solution such that the cathode does not make contact with the device. The electrically conductive device may thus act as the anode, such that when an electric current passes through the electrolyte (between the anode and cathode), the surface of the device is etched, i.e., the current will etch the exposed surface by "plating" the device material, acting as the anode in this case, toward the inserted cathode in an electrochemical etching process. The device may be made electrically conductive by attachment to an anode (i.e., wired in a circuit)

The cathode may be shaped to match the general contour of the surface to maintain constant distance and therefore constant resistance between the cathode and anode, or a simple geometric shaped cathode such as a cylinder may be used and compensated with an insulating coating or cover applied selectively to achieve constant resistance across the cathode-anode gap. Fine tuning of the concentration of electrolyte, current, and temperature may be used so that a standard shaped cathode may remove material in a specific and selected manner.

According to certain aspects of the present invention, the device and the cathode may be placed into a fixture having electrical connection(s) (i.e., electric leads that make contact with or are directly attached to the device and the cathode). The electrolyte solution may be pumped into and through the fixture so that there is a flow of electrolyte solution between the device (i.e., anode) and the cathode (i.e., the anode-cathode gap). According to certain aspects, the cathode may be part of the fixture such that only the implantable device needs to be positioned within the fixture.

In all cases, the electrolyte solution may be recirculated or circulated so that newly introduced electrolyte may be moved rapidly through the anode-cathode gap and out into an external tank so that the removed material flows out into a settling tank instead of plating to the inserted cathode. Alternatively, the removed material may simply be plated onto the cathode.

Thus, according to certain methods of the presently disclosed invention, the device is exposed to an electrolyte solution comprising an aqueous solution having an electrolyte dissolved therein. The electrolyte may be selected from the group consisting of a water-soluble inorganic compound, a water-soluble organic compound, an acid, a base, a water-soluble oxidizer, an alcohol, a glycol, a glycol ether, an amine, an amide, a pyrrolidone, and mixtures thereof.

According to certain aspects, a preferred electrolyte solution is one that comprises a water-soluble inorganic compound. Any suitable water-soluble inorganic compound can be used to form the electrolyte solution. Suitable water-soluble inorganic compounds include salts of Group Ia, IIa, transition metals, and mixtures thereof. Examples of suitable metals cations include; lithium, sodium, potassium, magnesium, and calcium. According to certain aspects, the water soluble inorganic compound may be selected from the group consisting of chlorides, such as sodium chloride (NaCl), potassium chloride (KCl), calcium chloride ($CaCl_2$), magnesium chloride ($MgCl_2$), and ammonium chloride ($NH_4Cl$); phosphates, such as dibasic sodium phosphate ($Na_2HPO_4$), monobasic sodium phosphate ($NaH_2PO_4$), monobasic potassium phosphate ($KH_2PO_4$), and dibasic potassium phosphate ($K_2HPO_4$); sulfates such as sodium sulfate ($Na_2SO_4$), potassium sulfate ($K_2SO_4$), and ammonium sulfate (($NH_4)_2SO_4$); nitrates such as sodium nitrate ($NaNO_3$), potassium nitrate ($KNO_3$), ammonium nitrate ($NH_4NO_3$), and potassium nitrite ($KNO_2$); bromides such as potassium bromide (KBr), sodium bromide (NaBr), ammonium bromide ($NH_4Br$), calcium bromide ($CaBr_2$), and magnesium bromide ($MgBr_2$); fluorides such as sodium fluoride (NaF), potassium fluoride (KF), and lithium fluoride (LiF), magnesium fluoride ($MgF_2$), and calcium fluoride ($CaF_2$); and mixtures thereof. Preferred electrolytes include NaCl, NaBr, NaF, KBr, KF, and KCl. Typically, the water-soluble inorganic compound is present in the electrolyte solution at a concentration of about 0.01M to saturation, such as from about 0.05M to about 10M, or from a concentration of about 0.05M to about 5M, or from a concentration of about 0.05M to about 3M.

Water soluble organic compounds can be used in preparing the electrolyte solution. Suitable water-soluble organic compounds include carbohydrates, including; tetroses such as erythrose, threose, and erythrulose; pentoses, such as ribose, arabinose, xylose, lyxose, ribulose, and xylulose; hexoses, such as allose, altrose, glucose, mannose, gulose, idose, galactose, talose, psiscose, fructose, sorbose, and tagatose; disaccharides, such as sucrose, lactose, maltose, trehalose, and cellobiose; oligosaccharides; polysaccharides; and mixtures thereof. In a preferred embodiment, the water-soluble organic compound is glucose. Typically, the water-soluble organic compound is present in the electrolyte solution at a concentration of about 0.0M to about 5M, preferably a concentration of about 0.05M to about 3M, and more preferably at a concentration of about 0.1M to about 1M.

The current and current density may be varied as well as the distance between the anode and the cathode, the concentration and temperature of the electrolytes, and flow rate of the electrolyte. This allows for optimization of the surface geometry at the nanometer scale to maximize cellular response and the rate of bone integration through manipulation of these various factors. By such manipulation, it is possible to create nanoscale surface geometries significantly superior to those of the prior art.

That is, a current may be applied and surface characteristics such as feature height, length and surface density (number of features in a given area) can be manipulated by adjustment of these various parameters. For example, the electrolyte type, i.e., salt solution, acid, alkaline, alcohol, or combinations of the preceding, and the electrolyte concentration may affect characteristics (i.e., depth, pattern, geometry) of the etched surface. According to a preferred embodiment, the electrolyte may be a salt solution, such as a salt solution having some level of acidity (e.g., aqueous solutions of NaCl, NaBr, NaF, KCl, KBr, or KF). In addition, the presence of other organic and/or inorganic additives can directly impact the desired features and their generation on the surface.

As mentioned, the current, voltage, and current density (rate of metal removal) may be varied, in addition to the temperature of the electrolyte solution. Such variation may affect the rate and amount of metal removal from the surface of the device (etch depth, which is differentiated over the nanoscale surface geometry). For example, the surface may be milled or removed to a depth of several mil (where 1 mil equals 25,400 nm). Additionally, the flow rate of the electrolyte, flow path of the electrolyte (e.g., flow direction, such as from the anode to the cathode or vice versa, or perpendicular to the plane of the anode and cathode, etc.), and the rate of recirculation of old electrolyte versus addition of new electrolyte may all affect the rate, pattern, and amount of material removed from the surface of the device. Other aspects, such as whether the electrical current is continuous or pulsed (direct) or pulsed (reversing), and the pulse period and duration will also affect the etch characteristics (e.g., surface geometry and pattern).

Finally, the surface design of the cathode tool (e.g., surface roughness, surface features, surface curvature, etc), and the distance between the electrodes (i.e., the electrolyte gap; from thousandths of an inch to a gap measured in inches) may be varied to change the etch characteristics.

One embodiment that achieves many of the desired surface characteristics on a wide variety of metal and metal alloys includes a mixture of one or more of NaCl, $NaNO_3$, NaBr, NaF, KCl, KBr, KF. For example, in an exemplary embodiment that works particularly well on cobalt chrome and alloys thereof includes from 0.5M to 10M of each of NaCl and $NaNO_3$, and less than 0.5M of NaF, such as 0.01 to 0.5M NaF, included in water to form an aqueous electrolyte solution. One embodiment that achieves many of the desired surface characteristics on both Grade 2 and Grade 5, and similar alloys, of titanium includes from 0.5M to 5M of each of NaCl, NaBr, and NaF included in water to form an aqueous electrolyte solution. In a specific exemplary embodiment, the electrolyte solution may comprise NaCl (1.5 lb./gal, about 3M), NaBr (1.0 lb./gal, about 1.2M), and NaF (0.02 lb./gal, about 0.06M) dissolved in deionized water.

The etching process is carried out by submersing the device in the electrolyte solution and passing a current between the cathode and the anode. The device may act as the anode, such as by connection of the anode to the device and positioning of the cathode in the electrolyte solution. The cathode may be positioned a specific distance from the device, i.e., an electrolyte gap. According to certain aspects, the electrolyte gap may be 0.05 to 1 inch (about 1.25 to 25.4 mm), such as 0.1 to 0.5 inches wide (about 2.54 to about 12.7 mm).

The electrochemical etching process is generally carried out at or near room temperature, such as from 15° C. to 30° C., or from 20° C. to 25° C., but elevated or reduced temperatures are also possible. The process may include use of a current density of from 5 to 100 DC Amps/in$^2$ surface and a voltage of 5 to 20 V DC, generally non-pulsed. The electrolyte flow rate, direction and path may vary depending on the product design. In general, a 98+% first pass separation of byproducts from electrolyte can be expected during recirculation of the electrolyte solution.

The amount of metal removed from the surface, i.e., depth of etch, is unlimited, but generally less than about 10 mil (about 254,000 nm), such as less than about 5 mils (about 127,000 nm), or about 0.01 mils to about 5 mils (about 254 nm to about 127,000 nm) and may depend on the amount of exposure time and current, as well as the flow rate and temperature of the electrolyte solution.

Pattern Generation

According to certain aspects of the present invention, portions of the implantable device may be etched, such as in a pattern. Those portions that are to remain un-etched may be protected from the etching composition using a masking material. Masking materials may include static adhesion films applied to the surfaces to be protected from the chemical etching compositions. Other masking materials may include at least coatings applied to the surfaces to be protected. The exposed, non-masked surfaces may then be etched by exposure to the etching compositions of the present invention.

For objects which are to be etched using a chemical etchant, the coating may be a coating resistant to the chemical etchant. Moreover, for objects that are to be etched using EChE, the coating may be an electrically non-conductive masking material or coating.

Coatings resistant to the chemical etching composition may be applied by any means known in the art, such as at least dipping, pouring, spraying, brushing, or rolling. Exemplary coatings resistant to the chemical etching compositions of the present invention include, for example, maskants from AC Products, such as ADCOAT AC-818.

Depending on the solids content of the selected coating, multiple applications of the coating may be necessary, allowing for sufficient drying time between applications. The coatings used are generally customized to protect the implantable device from the selected etchant while avoiding any harm to the underlying material of the object.

After each application, the coating may be allowed to cure in a manner which prevents damage to the preceding application, and/or which does not inhibit future applications. The term "cure", as used in connection with a cured coating, means that at least a portion of the components that form the coating are polymerized, cross-linked, or dried to form a hardened film. Curing or drying reactions to form the hardened film may be carried out under ambient conditions, or may be carried out at elevated temperatures, pressures, or in the presence of various gases. For example, the coating may comprise a solvent which may be evaporated to dry or cure the coating. The solvent evaporation may be accelerated by vacuum removal coupled with fresh air or inert gas supply. Depending upon the nature of the chosen coating, heat sources may be used to accelerate drying. Further, for certain coating chemistries, additional processing steps (imaging, hardening, fixing, etc.) may be necessary to make the coating fully resistant to the targeted etching solution.

The coating may be applied in a pattern that exposes the regions of the implantable device to be etched and covers the regions to be protected. Alternatively, the coating may be applied to a surface and patterned to remove those regions of the coating that are to be etched on the implantable device. Such removal may be via mechanical scribing and peeling, or by laser ablation, wherein a laser is utilized to remove or ablate the coating in specific regions or patterns. In both cases, a thickness of the coating may be matched to the characteristics of the scribing or laser ablation equipment. In general, the thinnest application that allows for full protection during the chemical etching step is desired, as thinner coatings require less drying time, less coating material, lower laser intensities, and less time stripping the coating after etching is complete. Moreover, for laser ablation processes, colorants or other additives may be added to the coating to improve the ablation process. The colorants and/or additives may be matched to the specific laser type and wavelength.

According to certain aspects, the coating may be a photoresist, wherein the photoresist may be applied to one or more surfaces, or portions thereof, of the device. A photoresist is a photosensitive coating that changes properties when exposed to light, either gaining or losing resistance to attack by an etchant or solvent in the areas exposed to electromagnetic radiation, most commonly in the UV light spectrum. The thickness and properties of the photoresist (e.g., positive or negative photoresist) may be matched to the equipment used for exposure of the pattern onto the photoresist.

While several methods for coating the surface of the implantable device have been described herein, other methods known in the art are within the scope of the present invention. Furthermore, more than one coating layer may be applied to the surface of the implantable device, wherein each coating layer may vary in thickness and identity of the coating material. As previously indicated, selection of the specific coating thickness and coating material may depend on at least the method of pattern generation to be used in future steps of the process.

The term "pattern generation" generally describes various methods and implementations used to remove a portion of the coating from the surface of the implantable device according to a specific pattern or design. The pattern may be preset or programmed into a computer (e.g., translated from CAD drawings) which directs the movements of the various devices used to remove the portion of coating and movements of the implantable device, either together or individually.

The patterned implantable device, whether produced through laser ablation, mechanical scribing and peeling, or by a photo resist process may be exposed to any of the acidic or alkaline chemical etching composition using any of the methods described above to provide a nanoscale surface geometry thereon.

Alternatively, the patterned implantable device may be exposed to an electrochemical etching solution, i.e., any of the aqueous electrolyte solutions described herein, and may have a current passed therethrough as described hereinabove. Generally, the implantable device may be exposed to the electrolyte solution through submersion in the solution.

The amount of material removed by the etching methods, i.e., depth of etch, is generally less than about 10 mil (about 254,000 nm), such as less than about 5 mils (about 127,000 nm), or about 0.01 mils to about 5 mils (about 250 nm to about 127,000 nm) and may depend on the amount of exposure time to the chemical or electrochemical etching composition and depletion of the chemistry in the composition, e.g., after long exposure times. The upper limit of etch depth depends only on the time, temperature, and chemistry (e.g., ratio and/or concentrations of various components; recirculation or replacement of chemistry) of the etch reaction. For the electrochemical etch process, the etch depth may also depend on factors specific to the electric current generation and/or application, e.g., the voltage, current density, electrolyte gap, etc.

The rate of etching, i.e., rate of material removed, may depend on a combination of the proportion of chemical components to one another, the temperature, the surface being etched (i.e., type of metal), and/or the amount of agitation of the implantable device in the chemical etching composition, or the flow rate of the circulating etching solution (e.g., electrolyte or chemical etching solution). For example, according to certain aspects of the presently disclosed methods, the implantable device may be etched at a rate of 0.1 to 2 mil/hour (about 30,500 nm). This rate can be greatly accelerated or slowed with changes in the exposure temperature (e.g., temperature of the implantable device, chemical etch composition, or both during the exposure reaction), and/or the concentration of components of the etch composition (e.g., greater concentration of the components). The rate of removal of material in the electrochemical process may also depend on factors specific to the electric current generation and/or application.

Nanoscale Surface Geometry

The nanoscale surface geometry imparted by the compositions and methods of the presently disclosed invention are distinguished from any geometry or pattern that may be applied using the maskants detailed above, or that may be provided on the substrate surface before the etching compositions are applied (e.g., certain implantable devices may comprise surface features provided by chemical or mechanical etching that are micrometers to millimeters in depth; see for example U.S. Pat. Nos. 5,258,098, 5,507,815, and 6,193,762).

Once etching is complete, the implantable device may be rinsed clean of all residual etchant. According to certain aspect, the implantable device is substantially free or totally free of residual etchant.

If the implantable device was coated on a portion thereof with a maskant or etch resistant coating, the maskant may be removed by placing the device in a bath of stripping solution (a solvent matched to the coatings) to remove all remaining coating material. According to certain aspects, the implantable device is substantially free or totally free of residual maskant. Alternatively, a wet blast process consisting of a high-pressure spray of a stripping solution could be used in place of the stripping solution to mechanically and chemically remove the coating from the object. After the remaining coating is removed ("stripping"), the implantable device may be thoroughly pressure-washed and dried in preparation for any required final surface treatments.

The chemical and/or electrochemical etching compositions and methods disclosed herein may provide a regular repeating, though non-identical, pattern having nanoscale geometry on a substrate surface. This pattern is an outcome of the chemical or electrochemical reactions of the inventive compositions disclosed herein and is not the result of a specifically applied pattern. Moreover, while any two areas of the etched surface may have the same surface roughness and topographical features, and thus may appear to have a regular repeating pattern, these patterns are not identical. While the etch depth is indicated above to be on the micrometer scale (e.g., generally less than 1 mil or 25.4 micrometers), the chemical or electrochemical etching compositions provide a geometry on the surface of the device that is on the nanometer scale (i.e., surface roughness and topographical features).

These surfaces have been found to improve osseointegration of bone contacting implantable devices. Without wishing to be bound by one particular theory, the nanoscale geometry may provide pores into which osteoblasts and supporting connective tissue can migrate. Thus, the compositions and methods disclosed herein provide an improved surface on an osteoid implant, such as on a surface that may contact an adjoining surface (i.e., bone), and may help to promote bone growth, fusion, and healing responses. Such implants can include any bone contacting device known in the medical and dental fields, such as a bone fixative device or dental implant. For example, surgical bone fixation devices such as screws, staples, rods, wires, and plates. The irregular surface into which the bone grows creates a natural joinder between the bone and the implant, which maximizes the surface area of the joined element and improves the structural stability and functional connection therebetween.

These surfaces have also been found to improve biocompatibility of tissue contacting implantable devices. For example, stents and valves that have the nanoscale surface geometry reduce the incidence of restenosis. Restenosis occurs when smooth muscle cells in the blood aggregate into clumps and cause the stent to become occluded. While drug-eluting coatings have been used to prevent clumping, recent data has found that these coatings are not a satisfactory solution (i.e., coated stents have been shown to cause blood clots several years after installation). A patient receiving a coated stent must use blood thinners to prevent formation of blood clots that may dislodge from the region of the stent and cause stroke or heart attack. Restenosis of a stent may be largely determined by whether the first layer of cells to grow on the surface of a stent are endothelial cells or smooth muscle cells.

The nanoscale surface geometry of the present invention preferably selects endothelial cells (e.g., from the blood stream) to grow on the inside surface of the stent or stent cover compared to other cell types (e.g., smooth muscle cells). Endothelial cells, as opposed to smooth muscle cells, may 'recognize' the surface structure by pattern matching and adhere. This pattern recognition step is a key element in many molecular biology processes. The implantable devices having nanoscale surface geometry, and the methods and compositions useful for forming the geometry, take advantage of this native molecular biological process to influence the adherence of one type of cell, e.g., endothelial cells, in preference to other types, e.g., smooth muscle cells. Thus, surface nanostructures may be used to selectively enhance adhesion of endothelial cells over smooth muscle cells.

The nanoscale surfaces provided by the compositions and methods disclosed herein are improved over those formed by the prior art acid etch methods. That is, when included on an implant, they demonstrate improved osseointegration and/or biocompatibility of the implant when compared to prior art implants having surfaces formed using acid etch methods. Prior art solutions for improving biocompatibility used coatings, such as nanoporous hydroxyapatite or nanoporous aluminum oxide, to provide improved endothelialization. However, preclinical studies have shown variability regarding the effectiveness of stents coated with nanoporous materials, and nanoparticle debris ejected from the stent surface has been observed. This debris could provoke inflammation and subsequent restenosis.

Accordingly, the present invention provides an improved implantable device comprising a body with at least one surface having a defined three-dimensional pattern created by the etching compositions and methods of the present invention.

Implantable Devices

Exemplary devices that may comprise the nanoscale surface geometry imparted by the compositions and methods of the presently disclosed invention include medical devices that are tissue contacting, such as an (auxiliary) artificial heart, an artificial valve, a stent, and a pacemaker. In the case of the (auxiliary) artificial heart, examples of the component of the device include a pump casing, an impeller, a shaft constituting the impeller, a rotor and a fin, and an inlet port and an outlet port communicating with the pump casing.

Exemplary devices that may comprise the nanoscale surface geometry imparted by the compositions and methods of the presently disclosed invention include any medical or dental implant for connection to, or positioning adjacent, living bone of a patient. For example, surgical bone fixation devices such as screws, staples, rods, and plates, and implants including at least medical implants such as spinal implants, limb prostheses, portions of a joint replacement device, cochlear prostheses, and dental implants.

Restorative implant dentistry generally involves the surgical restoration of one or more teeth in a patient's mouth using an osseointegrative dental implant or anchor that supports a prosthetic tooth (e.g., a porcelain crown), an implant-supported bridge or an implant-supported denture. Dental implants have traditionally been fabricated as a bone-anchoring pin or screw formed from a known osseointegrative material, such as a cobalt chrome alloy, stainless steel, etc. The bone-anchoring portion of the pin or screw is typically configured to extend into an osteotomy formed within the alveolar bone (either the maxilla or the mandible) of a patient. Biological healing and bone tissue growth around the surgical site eventually results in osseointegration (i.e., permanent fixation) of the implant with the living bone tissue surrounding the osteotomy and the implant. Other portions of the implant typically extend through the gingiva into the oral cavity to support one or more prosthetic teeth.

Accordingly, the present invention further provides dental implants comprising a body with at least one surface having a defined three-dimensional pattern created by the chemical or electrochemical etching compositions and methods of the present invention. The at least one surface having the etched pattern is positioned in contact with living bone of a patient, such as an alveolar bone. For example, the dental implant may include a core or anchor portion formed of cobalt chrome, and a head portion that extends from the anchor portion and has an abutment interface. The anchor portion generally includes the surface having a defined three-dimensional pattern disposed about the portion that interfaces with the alveolar bone. After implantation of the implant, such as by screwing or press-fitting the core into the bone (i.e., the osteotomy), bone tissue may osseointegrate into the surface having the defined three-dimensional pattern to anchor the implant in position within the surrounding bone. The head portion may provide an attachment point for the additional portions of the implant (e.g., a porcelain crown or denture).

As described, the anchor portion of the dental implant is positioned within the alveolar bone by press fitting or screwing. As such, the surface of the anchor portion of the dental implant may include either a smooth cylindrical form which is press-fit into a drilled osteotomy, or a threaded form which is threaded into a threaded or unthreaded osteotomy prepared using a bone drill, a bone tap and/or other specialized tools. The geometry of a threaded implant is typically such that it can be inserted into the osteotomy and firmly secured to the surrounding bone tissue via one or more threads which advance into the osteotomy. In a two-stage dental implant, as described above, the anchor and head portions may include addition portions, and may be formed of solid metal such as a cobalt chrome or alloy thereof or may be coated with a layer of cobalt chrome or alloy thereof.

Alternative dental implants include single-stage implants, wherein the tooth or prosthetic is integral with the anchor portion of the implant. In such a case, the entire implant may be formed of a ceramic or other appropriate material for a tooth or prostheses, and the anchor portion may include a coating or layer of solid metal such as cobalt chrome or alloy thereof on a surface thereof, wherein the metal coating includes the defined three-dimensional pattern.

The present invention further provides medical implants such a spinal implant, wherein the implant has a body comprising a surface and connections sized and shaped for placement into an intravertebral disc space. The surface has a defined three-dimensional pattern created by the chemical or electrochemical etching compositions and methods of the present invention. The implant thus provides a surface area of bone-contacting features that allow for and encourage in-growth of bone and proteinaceous materials and biological attachment to a biocompatible material i.e., integration. The three-dimensional surface morphology may incorporate overlapping patterns of features in two dimensions as well as different and independent dimensional depths for each of the features (etched to microscale depths with nanoscale features).

Other exemplary implants include at least prosthetic devices or implants intended for repair of a traumatic bone injury. For example, the chemical or electrochemical etching compositions and methods of the present invention can be applied to at least one surface of an implant intended for connection or replacement of any type of long bone, including the femurs, tibias and fibulas of the legs, the humeri, radii and ulnas of the arms, metacarpals and metatarsals of the hands and feet and the phalanges of the fingers and toes. Implants formed by these methods can be used in the field of prosthetic surgery, for example in case of hip, knee, ankle, shoulder, elbow or finger prostheses or joint replacement. Moreover, implants formed by these methods may find use in craniofacial prosthesis such as an artificial ear (ear prosthesis), maxillofacial reconstruction, eye (orbital prosthesis), or nose (nose prosthesis), bone anchored hearing conduction amplification (i.e., bone anchored hearing aid), and cyborg antenna or "eyeborg," which is a device that is implanted in the skull to perceive color through sound waves (sound conduction through bone).

It is generally believed that the three-dimensional surface of the implantable device determines its ultimate ability to integrate into the surrounding living bone. Without being limited by theory, it is hypothesized that the cumulative effects of at least implant composition, implant surface energy, and implant surface topography play a major role in the biological response to, and osseointegration of, the implantable device.

Various implant body shapes may be generated to allow for implantation at various body sites and through various access paths. The structures and surfaces are designed to work in concert to preserve bone structures, and to provide for sufficient bioactivity in each respective location. For example, when the implantable device is a spinal implant, the device may provide stability within the disc space and the graft containment axial column, and the shapes and textures of the bioactive surfaces may vary based on the implant insertion path, location within the disc space, and frictional characteristics of the surfaces Exemplary spinal implants include those shown in U.S. Pat. Nos. 8,262,737; 8,496,710; 8,585,765; and 10,111,753.

Moreover, the particular etchant reaction conditions and/or maskant utilized for a given attachment surface may be dictated by the base metal utilized for the implant. While a cobalt chrome implant is contemplated as the best mode of practice in the invention, it is to be specifically understood that any base metal may be utilized as the implanted material. A change in the base metal would necessitate a change in the maskant and etchant reaction conditions. No limitation is to be inferred from the specific examples provided in the detailed description.

EXAMPLES

Example I: Chemical Etching of a Cobalt Chromium Surface

Surfaces of the cobalt chromium implantable device that are to be etched are first activated by exposure to an activation solution for a short time period at room temperature, such as by submerging (e.g., dipping) or spraying the surface with the activation solution. An exemplary activation solution includes a 10%-100% (v/v) aqueous solution of concentrated hydrochloric acid, although many other mineral acids would provide substantially the same results. While the implantable device is still wet with the activation solution (e.g., within 120 seconds, or 60 seconds, or 30 seconds), it is exposed to the chemical etching compositions using any of the methods disclosed herein.

Because it is preferred to expose the implantable device to the chemical etch composition within a short time after exposure to the activation solution, such as when the implantable device is still wet with the activation solution, it is necessary to apply any coatings or patterning before the activation step. As such, if the implantable device is to be patterned, such as by including a coating to protect certain portions or surfaces of the implantable device, that coating should be applied before the surface is activated and/or etched.

Provided below are exemplary chemical etching compositions according to certain aspects of the presently disclosed invention.

(A): An exemplary chemical etching composition for the chemical dissolution of a cobalt chromium surface according to certain aspects of the presently disclosed invention includes constituents and amounts as shown in Table 1.

Temperature ranges for the above solutions are from about 20° C. to about 100° C., such as from about 30° C. to about 95° C., or from about 40° C. to about 95° C., or from about 50° C. to about 95° C., or from about 60° C. to about 95° C., or from about 65° C. to about 95° C., or from about 80° C. to about 90° C., or from about 82° C. to about 88° C.

The substrate may be exposed to the chemical etching composition for greater than 0 seconds to greater than several hours or days. According to certain preferred aspects, the substrate is exposed to the composition for 1 to 1000 minutes, such as 2 to 200 minutes, or 5 to 50 minutes. According to certain examples, the substrate was exposed to the composition for 5 to 50 minutes or even 20 to 35 minutes.

TABLE 1

| Component | Range | Set-Point at start of etching |
| --- | --- | --- |
| Iron (Fe) | 0-400 g/l | 115 g/l |
| Cobalt (Co) | 0-400 g/l | 0.2 g/l |
| Chromium (Cr) | 0.2-400 g/l | 3.3 g/l |
| Molybdenum (Mo) | 0.1-400 g/l | 1.2 g/l |
| Hydrochloric Acid (HCl) | 1-10N | 4.0N |
| Nitric Acid ($HNO_3$) | 0.05-2.0N | 0.5N |
| Hydrofluoric Acid (HF) | 0.1-2.0N | 1.0N |

While a cobalt chromium surface can be etched at many (or all) combinations of chemistry within the ranges above, at the preferred set-point conditions, uniform removal of material at up to 0.015" and beyond was achieved with no measurable IGA, making it a suitable solution for flight-critical aerospace components.

Removal of material from a cobalt chromium surface using the chemical etch composition and disclosed methods is predictable and repeatable, but unlike most other alloys, once the material is removed, it generally forms a stable passive surface layer that inhibits further etching without a suitable chemical or electrochemical re-activation of the surface, or disruption of the surface layer (such as by mechanical means, e.g., grit-blasting). Because of this passivation, processing is most easily and economically performed with full targeted removal taking place in one step.

This solution is suitable for Cobalt-Chromium-Molybdenum based alloys such as, but not limited to, ASTM F75 (Standard Specification for Cobalt-28Chromium-6Molybdenum Alloy Casting and Casting Alloy for Surgical Implants), ASTM F799 (Standard Specification for Cobalt-28Chromium-6Molybdenum Alloy Forgings for Surgical Implants), and ASTM F1537 (Standard Specification for Cobalt-28Chromium-6Molybdenum Alloys for Surgical Implants).

This solution is also suitable for Cobalt-Chromium alloys containing Nickel such as ASTM F90 (Standard Specification for Wrought Cobalt-20Chromium-15Tungsten-10Nickel Alloy for Surgical Implant Applications) and ASTM F562 (Standard Specification for Wrought 35Cobalt-35Nickel-20Chromium-10Molybdenum Alloy for Surgical Implant Applications).

(B): An exemplary inventive high-iron composition for etching a cobalt chromium surface is shown in Table 2. This composition was found to provide surface roughness (Ra) changes from a starting condition of approximately 400 μ-in (about 10 micrometers, μm) to a finished condition of approximately 125 μ-in (about 3 μm), with a surface material removal of 0.005 inches.

TABLE 2

| Component | Range | Set-Point at start of etching |
| --- | --- | --- |
| Iron (Fe) | 50-400 g/l | 175 g/l |
| Cobalt (Co) | 0-400 g/l | 5 g/l |

TABLE 2-continued

| Component | Range | Set-Point at start of etching |
|---|---|---|
| Chromium (Cr) | 0.2-400 g/l | 3 g/l |
| Molybdenum (Mo) | 0.1-400 g/l | 0.5 g/l |
| Hydrochloric Acid (HCl) | 1-10N | 4.5N |
| Nitric Acid (HNO$_3$) | 0.05-2.0N | 0.11N |
| Hydrofluoric Acid (HF) | 0.1-2.0N | 0.9N |

(C): An exemplary inventive iron-free, high-metals composition for etching a cobalt chromium surface is shown in Table 3. The composition was found to provide surface roughness (Ra) changes from a starting condition of approximately 250 μ-in (about 6.4 μm) to a finished condition of approximately 70 μ-in (less than 2 μm), with a surface material removal of 0.005 inches.

TABLE 3

| Component | Range | Set-Point |
|---|---|---|
| Iron (Fe) | 0 g/l | 0 g/l |
| Cobalt (Co) | 7-355 g/l | 81.7 g/l |
| Chromium (Cr) | 3-170 g/l | 35.8 g/l |
| Molybdenum (Mo) | 1-40 g/l | 7.5 g/l |
| Hydrochloric Acid (HCl) | 2-10N | 4.5N |
| Nitric Acid (HNO$_3$) | 0.05-0.8N | 0.11N |
| Hydrofluoric Acid (HF) | 0.1-1.3N | 0.9N |

The high metals chemical etch composition shown in Table 3 provides a ratio of metals in solution that is at or near the ratio of the elemental components in the starting alloy, cobalt chromium molybdenum ASTM F75. The present inventors have found that increased metal concentrations reduce the surface roughness (i.e., in the micrometer scale) exponentially up to the point of saturation. Higher concentrations were found to decrease the rate of etch (i.e., as the metals concentrations rise, the rate of etching will begin to decrease, potentially making the processing of parts at or near full saturation impractical from a processing time standpoint).

(D): An exemplary inventive composition comprising component metals in their native ratios for etching a cobalt chrome surface is shown in Table 4. The total metals component of the etching solution is 210 g/l.

TABLE 4

| Component | Range | Set-Point |
|---|---|---|
| Iron (Fe) | 0-400 g/l | 30 g/l |
| Cobalt (Co) | 0-400 g/l | 180 g/l total |
| Chromium (Cr) | 0.2-400 g/l | component metals‡ |
| Molybdenum (Mo) | 0.1-400 g/l | |
| Hydrochloric Acid (HCl) | 1-10N | 5.9N |
| Nitric Acid (HNO$_3$) | 0.05-2.0N | 0.15N |
| Hydrofluoric Acid (HF) | 0.1-2.0N | 0.72N |

‡For a cobalt-molybdenum-chromium alloy, the composition includes: 117.6 g/l Co, 51.6 g/l Cr, and 10.8 g/l Mo.

The solution was heated to 180° F. (82.2° C.) and the activated substrate was added to the solution, which was maintained at a temperature of 173° F. to 177° F. (78° C. to 80.5° C.). The high metals chemical etch composition shown in Table 4 provides a ratio of metals in solution that is at or near the ratio of the elemental components in the starting alloy, cobalt chromium molybdenum ASTM F75.

(E): An exemplary inventive composition comprising component metals in their native ratios for etching a cobalt chrome surface is shown in Table 5. The total metals component of the etching solution is 140 g/l.

The solution was heated to 180° F. (82.2° C.) and the activated substrate was added to the solution, which was maintained at a temperature of 173° F. to 177° F. (78° C. to 80.5° C.). The high metals chemical etch composition shown in Table 5 provides a ratio of metals in solution that is at or near the ratio of the elemental components in the starting alloy, cobalt chromium molybdenum ASTM F75.

TABLE 5

| Component | Range | Set-Point |
|---|---|---|
| Iron (Fe) | 0-400 g/l | 20 g/l |
| Cobalt (Co) | 0-400 g/l | 120 g/l total |
| Chromium (Cr) | 0.2-400 g/l | component metals‡ |
| Molybdenum (Mo) | 0.1-400 g/l | |
| Hydrochloric Acid (HCl) | 1-10N | 7.1N |
| Nitric Acid (HNO$_3$) | 0.05-2.0N | 0.156N |
| Hydrofluoric Acid (HF) | 0.1-2.0N | 0.723N |

‡For a cobalt-molybdenum-chromium alloy, the composition includes: 78.4 g/l Co, 34.4 g/l Cr, and 7.2 g/l Mo.

(F): An exemplary inventive composition comprising component metals in their native ratios for etching a cobalt chrome surface is shown in Table 6. The total metals component of the etching solution is 200 g/l.

TABLE 6

| Component | Range | Set-Point |
|---|---|---|
| Iron (Fe) | 0-400 g/l | 80 g/l |
| Cobalt (Co) | 0-400 g/l | 120 g/l total |
| Chromium (Cr) | 0.2-400 g/l | component metals |
| Molybdenum (Mo) | 0.1-400 g/l | |
| Hydrochloric Acid (HCl) | 1-10N | 7.1N |
| Nitric Acid (HNO$_3$) | 0.05-2.0N | 0.156N |
| Hydrofluoric Acid (HF) | 0.1-2.0N | 0.723N |

‡For a cobalt-molybdenum-chromium alloy, the composition includes: 78.4 g/l Co, 34.4 g/l Cr, and 7.2 g/l Mo.

The solution was heated to 180° F. (82.2° C.) and the activated substrate was added to the solution, which was maintained at a temperature of 173° F. to 177° F. (78° C. to 80.5° C.). The high metals chemical etch composition shown in Table 6 provides a ratio of metals in solution that is at or near the ratio of the elemental components in the starting alloy, cobalt chromium molybdenum ASTM F75.

(G): An exemplary inventive composition comprising component metals in their native ratios for etching a cobalt chrome surface is shown in Table 7. The total metals component of the etching solution is between 140 g/l-210 g/l. The solution was heated to 180° F. (82.2° C.) and the activated substrate was added to the solution, which was maintained at a temperature of 173° F. to 177° F. (78° C. to 80.5° C.). The low component metals and high iron chemical etch composition shown in Table 7 provides a ratio of metals in solution that is at or near the ratio of the elemental components in the starting alloy, cobalt chromium molybdenum ASTM F75.

TABLE 7

| Component | Range | Set-Point |
|---|---|---|
| Iron (Fe) | 0-400 g/l | 120-170 g/l |
| Cobalt (Co) | 0-400 g/l | 20-40 g/l total |
| Chromium (Cr) | 0.2-400 g/l | component metals |
| Molybdenum (Mo) | 0.1-400 g/l | |
| Hydrochloric Acid (HCl) | 1-10N | 4-8N |

TABLE 7-continued

| Component | Range | Set-Point |
|---|---|---|
| Nitric Acid (HNO$_3$) | 0.05-2.0N | 0.1-0.3N |
| Hydrofluoric Acid (HF) | 0.1-2.0N | 0.65-0.85N |

Superior surface results were found for etching compositions comprising increasing iron concentrations and moderate concentrations of component metals at the ratios native to the original alloy. This is an important finding as it provides a processing composition that does not require the addition of non-native metals or metal salts. That is, the composition can be initiated at low concentrations of the component metals which may concentrate during etching and may aid in providing an improved surface finish, i.e., simply by etching more material while maintaining the appropriate acid concentrations. This greatly aids process control (i.e., the metals will always drift towards the alloy concentrations with increased usage).

Thus, according to certain aspects, a chemical etching composition of the presently disclosed invention may that achieve uniform removals with excellent surface finish includes moderate concentrations of native metals, up to saturation, at the elemental ratios present in the material of the parts being etched. It should be noted that nitric acid concentrations are relatively low for these compositions as high metals may lead to rapid breakdown of the nitric acid when that acid is present in higher concentrations.

As indicated, the chemical etch compositions of the presently disclosed invention provide uniform material removal of up to 0.015" and beyond with no measurable IGA, making them suitable compositions for etching flight critical aerospace components.

Example II: Chemical Etching of a Nitinol Surface

An exemplary chemical etching composition for the chemical dissolution of a nitinol surface according to certain aspects of the presently disclosed invention includes constituents and amounts as shown in Table 8.

TABLE 8

| Component | Range | Set-Point |
|---|---|---|
| Iron (Fe) | 0-225 g/l | 50 g/l-150 g/l |
| Titanium (Ti) | 0-saturation | 3.5 g/l-90 g/l |
| Nickel (Ni) | 0-saturation | 3.5 g/l-90 g/l |
| Hydrofluoric Acid (HF) | 0.1-43N | 0.5-3.5N |
| Nitric Acid (HNO$_3$) | 0-15N | 0.1-3N |

Example III: Chemical Etching of a Zirconia Surface

An exemplary chemical etching composition for the chemical dissolution of a zirconia surface according to certain aspects of the presently disclosed invention includes constituents and amounts as shown in Table 9.

TABLE 9

| Component | Range | Set-Point |
|---|---|---|
| Iron (Fe) | 0-225 g/l | 50 g/l-150 g/l |
| Zirconia (ZnO$_2$) | 0-saturation | 3.5 g/l-90 g/l |
| Hydrofluoric Acid (HF) | 0.1-43N | 0.5-3.5N |
| Nitric Acid (HNO$_3$) | 0-15N | 0.1-3N |

Example IV. Chemical Etching of a Stainless-Steel Surface

An exemplary chemical etching composition for the chemical dissolution of a surface composed of a 316 alloy of stainless-steel according to certain aspects of the presently disclosed invention includes constituents and amounts as shown in Table 10.

While a specific alloy of stainless steel is described with reference to example IV, other alloys of stainless steel may be etched with the compositions disclosed herein. These compositions may comprise a similar or the same acid composition as shown in Table 10 and may include component metals of the alloy being etched.

TABLE 10

| Component | Range | Set-Point |
|---|---|---|
| Iron (Fe) | 0-225 g/l | 50 g/l-225 g/l |
| Chromium (Cr) | 0-saturation | 3.5 g/l-90 g/l |
| Molybdenum (Mo) | 0-saturation | 3.5 g/l-90 g/l |
| Nickel (Ni) | 0-saturation | 3.5 g/l-90 g/l |
| Hydrochloric Acid (HCl) | 0.3-12N (1-37%) | 1.2N-3.0N (4.3-10.5%) |
| Nitric Acid (HNO$_3$) | 0-15N (0-67%) | 2.0N-4.0N (11.8-22.2%) * |
| Phosphoric Acid (H$_3$PO$_4$) | 0-3N (0-10%) | 0.1-0.3N (0.3-1.0%) |
| Hydrofluoric Acid (HF) | 0-43N (0-70%) | 0.1-0.3N (0.2-0.6%) |

* Total nitrates in the composition is the sum of the nitric acid and any metal nitrates or chemical intermediates containing nitrates. The mass percentages are illustrative of a solution where all the nitrates are contributed by the nitric acid in the solution.

Example V. Chemical Etching of a Titanium Surface

An exemplary chemical etching composition for the chemical dissolution of a titanium surface according to certain aspects of the presently disclosed invention includes constituents and amounts as shown in Table 11.

Temperature ranges for the above solutions are from about 15.5° C. to about 138° C., such as about 80° C. to about 93° C., for time periods of up to 100 hours, such as at least 1 minute to 10 hours, or from 10 minutes to 60 minutes.

TABLE 11

| Component | Range | Set-Point |
|---|---|---|
| Iron (Fe) | 0.1-500 ppm | 70-180 ppm |
| Titanium (Ti) | 0-100,000 ppm | 0.1-7,000 ppm |
| Metal Hydroxide | 5-75 wt. % | 18-30 wt. % |
| Amine | 0.1-40 wt. % | 2-10 wt. % |
| Chelating agent | 0.1-40 wt. % | 2-10 wt. % |

* When the total metals content equals 100 ppm, it may be provided by either the iron and/or the titanium, i.e., if 100 ppm iron is included, the titanium may be absent, and vice versa.

Example VI: Chemical Etching of an Aluminum Surface

An exemplary chemical etching composition for the chemical dissolution of an aluminum surface according to certain aspects of the presently disclosed invention includes constituents and amounts as shown in Table 12.

TABLE 12

| Component | Range | Set-Point |
|---|---|---|
| Iron (Fe) | 0-500 ppm | 70-180 ppm |
| Aluminum (Al) | 0-100,000 ppm* | 100-7,000 ppm |

TABLE 12-continued

| Component | Range | Set-Point |
|---|---|---|
| Metal Hydroxide | 5-75 wt. % | 18-30 wt. % |
| Amine | 0.1-40 wt. % | 2-10 wt. % |
| Chelating agent | 0.1-40 wt. % | 2-10 wt. % |

*When the total metals content equals 100 ppm, it may be provided by either the iron and/or the aluminum, i.e., if 100 ppm iron is included, the aluminum may be absent, and vice versa.

Temperature ranges for the above solutions are from about 15.5° C. to about 138° C., such as about 80° C. to about 93° C., for time periods of up to 100 hours, such as at least 1 minute to 10 hours, or from 10 minutes to 60 minutes.

Example VII: Electrochemical Etching of a Metal or Metal Alloy Surface

Desired surface characteristics on various metals and metal alloys can also be achieved using an electrolyte solution that includes a mixture of one or more of sodium chloride (NaCl), potassium chloride (KCl), calcium chloride ($CaCl_2$), magnesium chloride ($MgCl_2$), ammonium chloride ($NH_4Cl$), dibasic sodium phosphate ($Na_2HPO_4$), monobasic sodium phosphate ($NaH_2PO_4$), monobasic potassium phosphate ($KH_2PO_4$), dibasic potassium phosphate ($K_2HPO_4$), sodium sulfate ($Na_2SO_4$), potassium sulfate ($K_2SO_4$), ammonium sulfate (($NH_4)_2SO_4$), sodium nitrate ($NaNO_3$), potassium nitrate ($KNO_3$), ammonium nitrate ($NH_4NO_3$), potassium nitrite ($KNO_2$), potassium bromide (KBr), sodium bromide (NaBr), ammonium bromide ($NH_4Br$), calcium bromide ($CaBr_2$), magnesium bromide ($MgBr_2$), sodium fluoride (NaF), potassium fluoride (KF), lithium fluoride (LiF), magnesium fluoride ($MgF_2$), calcium fluoride ($CaF_2$). Preferred electrolytes include NaCl, $NaNO_3$, and NaF. Typically, the water-soluble inorganic compound is present in the electrolyte solution at a concentration of about 0.01M to saturation, such as from about 0.05M to about 10M, or from a concentration of about 0.05M to about 5M, or from a concentration of about 0.05M to about 3M.

For example, in an exemplary embodiment, from 0.5M to 10M of each of NaCl, $NaNO_3$, and NaF are included in water to form the aqueous electrolyte solution. A specific exemplary embodiment is shown in Table 13 below, which is suitable for the electrochemical dissolution of a cobalt chromium surface according to certain aspects of the presently disclosed invention.

TABLE 13

| Component | Range | Preferred Set-Point |
|---|---|---|
| NaCl | 0.01-6.5M | 2.0M |
| $NaNO_3$ | 0.01-8.5M | 1.4M |
| NaF | 0.01-0.5M | 0.06M |

A specific exemplary embodiment is shown in Table 14 below, which is suitable for the electrochemical dissolution of a titanium surface according to certain aspects of the presently disclosed invention.

TABLE 14

| Component | Range | Preferred Set-Point |
|---|---|---|
| NaCl | 0.01-6.5M | 3.0M |
| $NaNO_3$ | 0.01-8.5M | 1.2M |
| NaF | 0.01-0.5M | 0.6M |

While the presently disclosed invention has been described in detail, it should be appreciated by those skilled in the art that various modifications and alternations and applications could be developed in light of the overall teachings of the disclosure. Accordingly, the particular systems and methods disclosed are meant to be illustrative only and not limiting as to the scope of the invention.

What is claimed is:

1. A composition for etching a nanoscale geometry into a surface of a body implantable device formed of a metal or metal alloy, the composition comprising:
    1.2N-3.0N hydrochloric acid (HCl), 2.0N-4.0N nitric acid ($HNO_3$), 0.1N-0.3N phosphoric acid ($H_3PO_4$), 0.1N-0.3N hydrofluoric acid (HF), and
    component metals of the body implantable device, wherein the metal or metal alloy of the body implantable device comprises stainless steel, and the composition comprises 3.75 g/l-90 g/l of each of chromium (Cr), molybdenum (Mo), and nickel (Ni), and up to 225 g/l iron (Fe),
    wherein the body implantable device is a bone-contacting device and the nanoscale geometry enhances osseointegration when the bone-contacting device is implanted adjacent living bone, or
    wherein the body implantable device is a tissue-contacting device and the nanoscale geometry enhances endothelial attachment and proliferation when the tissue-contacting device is implanted adjacent tissue.

2. The composition of claim 1, comprising the component metals Cr, Mo, and Ni provided in a relative ratio that corresponds to a ratio of the metals in the stainless steel.

3. A composition for etching a nanoscale geometry into a surface of a body implantable device formed of a metal or metal alloy, the composition comprising:
    0.5N-3.5N hydrofluoric acid (HF) and 0.1N-3.0N nitric acid ($HNO_3$), and
    component metals of the body implantable device, device, wherein the metal or metal alloy of the body implantable device comprises a nickel-titanium alloy, and the composition comprises: 3.75 g/l-90 g/l of each of nickel (Ni) and titanium (Ti),
    wherein the body implantable device is a bone-contacting device and the nanoscale geometry enhances osseointegration when the bone-contacting device is implanted adjacent living bone, or
    wherein the body implantable device is a tissue-contacting device and the nanoscale geometry enhances endothelial attachment and proliferation when the tissue-contacting device is implanted adjacent tissue.

4. The composition of claim 3, wherein the nickel (Ni) and titanium (Ti) are provided in a relative ratio that corresponds to a ratio of the metals in the nickel-titanium alloy.

5. The composition of claim 3, wherein the composition further comprises: up to 225 g/l iron (Fe).

6. A composition for etching a nanoscale geometry into a surface of a body implantable device formed of a metal or metal alloy, the composition comprising:
    0.5N-3.5N hydrofluoric acid (HF) and 0.1N-3.0N nitric acid ($HNO_3$), and
    component metals of the body implantable device, wherein the metal or metal alloy of the body implantable device comprises a nickel-chromium-molybdenum alloy, and the composition comprises: 3.75 g/l-90 g/l of each of chromium (Cr), and molybdenum (Mo), and up to 225 g/l iron (Fe), wherein the body implantable device is a bone-contacting device and the nanoscale geometry enhances osseointegration when the bone-contacting device is implanted adjacent living bone, or wherein the body implantable device is a tissue-contacting device and the nanoscale geometry enhances endothelial attachment and proliferation when the tissue-contacting device is implanted adjacent tissue.

7. The composition of claim 6, wherein the nickel (Ni), chromium (Cr), and molybdenum (Mo) are provided in a relative ratio that corresponds to a ratio of the metals in the nickel-chromium-molybdenum alloy.

8. A composition for etching a nanoscale geometry into a surface of a body implantable device formed of zirconia, the composition consisting of:

0.5N-3.5N hydrofluoric acid (HF) and 0.1N-3.0N nitric acid ($HNO_3$), and soluble zirconia ($ZnO_2$) and up to 225 g/l iron (Fe), wherein the body implantable device is a bone-contacting device and the nanoscale geometry enhances osseointegration when the bone-contacting device is implanted adjacent living bone, or wherein the body implantable device is a tissue-contacting device and the nanoscale geometry enhances endothelial attachment and proliferation when the tissue-contacting device is implanted adjacent tissue.

9. The composition of claim 8, comprising 3.75 g/l-90 g/l of the soluble zirconia ($ZnO_2$).

10. A method for etching a nanoscale surface geometry on at least a portion of a body implantable device, the method comprising:

preparing a chemical etching composition according to claim 1; and contacting at least a portion of a surface of the implantable device with the chemical etching composition at a reaction temperature of from about 20° C. to about 100° C., wherein the surface of the body implantable device comprises stainless steel.

11. The method of claim 10, further comprising, before the step of contacting with the chemical etching composition:

activating the surface to be etched with an activation solution comprising a 10% to 100% (v/v) aqueous solution of a mineral acid.

12. The method of claim 11, wherein the activating step is carried out within 120 seconds before the contacting.

13. The method of claim 10, wherein the body implantable device is an implantable bone-contacting device, and the nanoscale surface geometry enhances osseointegration when the bone-contacting device is implanted adjacent living bone, or wherein the body implantable device is an implantable tissue-contacting device and the nanoscale surface geometry enhances endothelial attachment and proliferation when the tissue-contacting device is implanted adjacent tissue.

14. A method for etching a nanoscale surface geometry on at least a portion of a body implantable device, the method comprising:

preparing a chemical etching composition according to claim 3; and contacting at least a portion of a surface of the implantable device with the chemical etching composition at a reaction temperature of from about 20° C. to about 100° C., wherein the surface of the body implantable device comprises a nickel-titanium alloy.

15. The method of claim 14, further comprising, before the step of contacting with the chemical etching composition:

activating the surface to be etched with an activation solution comprising a 10% to 100% (v/v) aqueous solution of a mineral acid.

16. A method for etching a nanoscale surface geometry on at least a portion of a body implantable device, the method comprising:

preparing a chemical etching composition according to claim 6; and contacting at least a portion of a surface of the implantable device with the chemical etching composition at a reaction temperature of from about 20° C. to about 100° C., wherein the surface of the body implantable device comprises a nickel-chromium-molybdenum alloy.

17. The method of claim 16, further comprising, before the step of contacting with the chemical etching composition:

activating the surface to be etched with an activation solution comprising a 10% to 100% (v/v) aqueous solution of a mineral acid.

18. A method for etching a nanoscale surface geometry on at least a portion of a body implantable device, the method comprising:

preparing a chemical etching composition according to claim 9; and contacting at least a portion of a surface of the implantable device with the chemical etching composition at a reaction temperature of from about 20° C. to about 100° C., wherein the surface of the body implantable device comprises a nickel-chromium-molybdenum alloy.

19. The method of claim 16, further comprising, before the step of contacting with the chemical etching composition:

activating the surface to be etched with an activation solution comprising a 10% to 100% (v/v) aqueous solution of a mineral acid.

* * * * *